(12) United States Patent
Romero et al.

(10) Patent No.: US 9,528,084 B2
(45) Date of Patent: Dec. 27, 2016

(54) SYSTEM FOR COOLING PRETREATED BIOMASS PRIOR TO MIXING WITH ENZYMES

(71) Applicant: Andritz Inc., Glens Falls, NY (US)

(72) Inventors: Rodolfo Romero, Gansevoort, NY (US); Bertil Stromberg, Diamond Point, NY (US); Allen Turner, Alpharetta, GA (US)

(73) Assignee: Andritz Inc., Glens Falls, NY (US)

( * ) Notice: Subject to any disclaimer, the term of this patent is extended or adjusted under 35 U.S.C. 154(b) by 0 days.

(21) Appl. No.: 14/426,889

(22) PCT Filed: Sep. 10, 2013

(86) PCT No.: PCT/US2013/058789
§ 371 (c)(1),
(2) Date: Mar. 9, 2015

(87) PCT Pub. No.: WO2014/039986
PCT Pub. Date: Mar. 13, 2014

(65) Prior Publication Data
US 2015/0240198 A1    Aug. 27, 2015

Related U.S. Application Data

(60) Provisional application No. 61/722,514, filed on Nov. 5, 2012, provisional application No. 61/698,877, filed on Sep. 10, 2012.

(51) Int. Cl.
*C12M 1/00* (2006.01)
*C12M 1/40* (2006.01)
(Continued)

(52) U.S. Cl.
CPC ............ *C12M 45/09* (2013.01); *C12M 21/18* (2013.01); *C12M 33/04* (2013.01); *C12M 41/12* (2013.01);
(Continued)

(58) Field of Classification Search
CPC ....... C12M 21/18; C12M 33/04; C12M 41/12; C12M 41/26; C12M 45/06; C12M 45/09; C12M 45/20; C12P 19/14; Y02E 50/16
See application file for complete search history.

(56) References Cited

U.S. PATENT DOCUMENTS

| | | | |
|---|---|---|---|
| 8,617,355 B2 | 12/2013 | Romero | |
| 2009/0098616 A1 | 4/2009 | Burke et al. | |
| 2010/0255554 A1 | 10/2010 | Benson et al. | |

FOREIGN PATENT DOCUMENTS

| | | |
|---|---|---|
| CN | 1010855358 A | 10/2010 |
| WO | 2009046537 | 4/2009 |

OTHER PUBLICATIONS

The State Intellectual Property Office of the People's Republic of China, Notification of First Office Action, Sep. 25, 2015, pp. 1-10, Beijing.

(Continued)

*Primary Examiner* — Nathan Bowers
*Assistant Examiner* — Lydia Edwards
(74) *Attorney, Agent, or Firm* — Kerri A. Hochgesang; Robert Joseph Hornung

(57) ABSTRACT

A method to treat biomass, e.g., lignocellulosic material, including: performing a pretreatment step on the biomass and discharging the pretreated biomass; in at least a first enzymatic hydrolysis reactor producing a liquefaction material, recirculating at least a portion of the liquefaction material from the at least first reactor to a location upstream of the addition of the enzymes as at least a portion of the coolant for the hot pretreated biomass.

12 Claims, 11 Drawing Sheets

(51) Int. Cl.
  *C12P 19/14* (2006.01)
  *C12M 1/26* (2006.01)
  *C12M 1/34* (2006.01)
(52) U.S. Cl.
  CPC ............ *C12M 41/26* (2013.01); *C12M 45/06* (2013.01); *C12M 45/20* (2013.01); *C12P 19/14* (2013.01); *Y02E 50/16* (2013.01)

(56) References Cited

OTHER PUBLICATIONS

Zheng, Yi, et al., Overview of Biomass Pretreatment for Cellulosic Ethanol Production, Int. J. Agric & Biol. Eng., 2009, pp. 51-68, vol. 2, No. 3., United States.

SYSTEM FOR COOLING PRETREATED BIOMASS PRIOR TO MIXING WITH ENZYMES

CROSS REFERENCE TO RELATED PATENT APPLICATIONS

This application is related to, and claims the benefit of, U.S. Provisional Patent Application No. 61/698,877, filed Sep. 10, 2012, U.S. Provisional Patent Application No. 61/722,514, filed Nov. 5, 2012, and PCT International Application No. PCT/US2013/058,789, filed Sep. 9, 2013. Each of the above-identified priority patent applications is incorporated herein by reference in its entirety.

BACKGROUND

The term "biomass" generally relates to any material that is derived from living, or recently living biological organisms. In the energy context it is often used to refer to plant material, however by-products and waste from livestock farming, food processing and preparation and domestic organic waste, can all form sources of biomass. Biomass is widely available and contains a high proportion of cellulose, hemicellulose and lignin. The four main categories of biomass are: (1) wood residues (including sawmill and paper mill discards), (2) municipal paper waste, (3) agricultural residues (including corn stover and corn cobs and sugarcane bagasse), and (4) dedicated energy crops (which are mostly composed of fast growing tall, woody grasses such as switch grass and Miscanthus). Lignocellulosic biomass contains three primary polymers that make up plant cell walls, namely, (1) cellulose, a polymer of D-glucose; (2) hemicellulose which contains two different polymers i.e. xylan, a polymer of xylose and glucomannan, a polymer of glucose and mannose; and (3) lignin, a polymer of guaiacyl propane and syringyl propane units. Of these components cellulose is believed to be most desirable since it can be converted into monomer glucose that can be fermented to ethanol.

The exemplary embodiments described herein relate generally to the field of enzymatic conversion, also known as enzymatic hydrolysis, of biomass, (e.g., lignocellulosic material) to obtain monomeric sugars and particularly to maximizing enzyme performance/effectiveness during a liquefaction stage of pretreated biomass.

The production of ethanol from biomass generally entails the following steps: (1) collection and transportation of the biomass to a processing plant; (2) pretreatment of the biomass (pre-hydrolysis) with steam explosion, chemicals (e.g., with or without the addition of an acid or a base), physical means, biological means, and the like; (3) performance of enzymatic hydrolysis using highly specialized enzymes that catalyze the depolymerization of the cellulose into glucose; (4) fermentation of the glucose to ethanol; and (5) separation of the ethanol from the aqueous fermentation broth. Ultimately the separation step removes the last remaining water making a water free ethanol suitable for blending with gasoline.

Several techniques for the pretreatment of biomass material have been explored with the aim of producing substrate that can be more rapidly and efficiently hydrolyzed to yield fermentable sugars. See, e.g., Zheng, Yi, et al., "Overview of Biomass Pretreatment for Cellulosic Ethanol Production," *Int. J. Agric & Biol. Eng* ., Vol. 2, No. 3, pp. 51-68 (2009). These approaches have in common the use of conditions and procedures that are designed to increase the surface area to which reactants and enzymes have access. In the case of pretreatment using steam explosion, biomass is fiberized and the cellulose is fractured. To drive the reactions between the enzymes and the pretreated biomass, in particular operating temperature ranges must exist.

Prior to enzymatic hydrolysis of biomass, the biomass may undergo pretreatment involving one or more of the following: acidic condition hydrolysis (with or without the addition of acid), steam explosion, other pretreatment such as ammonium hydrolysis, lime hydrolysis, etc., In particular it may be necessary to cool the pretreated biomass to enhance the enzyme performance during the enzymatic hydrolysis (liquefaction) stage of processing.

For example, biomass, such as lignocellulosic material, may be pretreated to make the sugar based polymers, such as hemi-cellulose and cellulose, accessible to enzymes. After being pretreated, the biomass is processed in an enzymatic hydrolysis reactor vessel(s) where enzymes hydrolyze, e.g., break down, the hemi-cellulose and cellulose polymers to monomers. The pretreated biomass tends to be highly viscous. During enzymatic hydrolysis, the pretreated biomass is liquefied as the polymers of the pretreated biomass are converted to monomers. The monomers, sugars, are further processed into ethanol, butanol or other sugar based products.

Enzymatic hydrolysis of pretreated biomass poses many challenges. These challenges range from the interaction of the enzymes themselves with the biochemical complexity of the pretreated biomass and its derivatives to the physical characteristics of the liquid/fiber, monomeric/oligomeric mixture (collectively referred to as "slurry") and its rheological features.

Conventional reactors used to perform continuous enzymatic hydrolysis (a process where there are both input and output flows to the process, but the reaction volume is kept constant) required large tanks having expensive and powerful impellers to mix the enzymes into the slurry. Enzymatic hydrolysis or liquefaction of biomass may require several hours, typically more than twelve (12) hours, of mixing in the large tanks. The mixing process reduces the apparent viscosity of the biomass by converting the biomass from a generally solids composition to a liquefied slurry. The pretreated biomass typically starts the mixing process having a semi-solid, mud-like consistency.

Additional conventional enzymatic hydrolysis systems include batch and fed-batch processes. In a batch process, all the components (including pH-controlling substances) are placed in a reactor vessel at the beginning of the enzymatic hydrolysis. During the enzymatic hydrolysis process of the biomass, there is no input into or output from the reactor vessel. An alternative batch process is a fed-batch process. In a fed-batch process (as described in U.S. Patent Publication No. 2010/0255554 A1) nothing is removed from the reactor vessel during the process, but one substrate component is progressively added in order to control the reaction rate by the concentration of the substrate. The substrate is fed continuously into the reactor over the enzymatic hydrolysis period without withdrawing any hydrolysate until the process is complete (as is the case with a batch process).

Biomass is pretreated and subsequently subjected to enzymatic hydrolysis resulting in the conversion to monomeric sugars. The enzymes added to the pretreated biomass typically have a relatively low concentration with respect to the solids content of the pretreated biomass. The pretreated biomass and enzyme mixture tends to be highly viscous as it enters a mixing and enzymatic hydrolysis reactor system. The high apparent viscosity of the mixture has motivated the use of relatively small reactor vessels to reduce the torque needed to mix the mixture while in the reactor vessels. Such a system typically includes one or more enzymatic hydrolysis reactor vessels. The temperature within the enzymatic hydrolysis reactor vessel(s) is important to allow for proper activity of the enzymes. Enzymes typically require a temperature environment of 20° C. (Celsius) to 65° C. Higher temperatures can cause damage to the enzymes, therefore temperature level and temperature level control are important requirements in and around the reactor. The commonly anticipated time span in industrial applications for enzymatic hydrolysis reaction/retention is at least 48 hours, more typically at least 72 hours.

Another challenge in conventional biomass treatment systems is to cool the pretreated biomass to a temperature suited to enzymatic hydrolysis. By way of example, there is a need to cool pretreated biomass from a high temperature, such as 100° C., at the discharge of a pretreatment vessel, to a substantially cooler temperature, such as 20° C. to 65° C., before the biomass enters the reactor vessel(s) for enzymatic hydrolysis.

A conventional enzymatic hydrolysis reactor system is described in U.S. Patent Publication No. 2012/0125549 and discloses adding cold water to the pretreated biomass material that has been subjected to steam explosion in order to reduce the temperature of the pretreated biomass from about 100° C. to the more enzymatically conducive temperature of 40° C. to 50° C. prior to being transferred to an enzymatic hydrolysis reactor vessel. Large volumes of cold water must be added to the hot pretreated biomass to achieve the desired lower temperature, as well as a favorable total solids consistency for successful enzymatic hydrolysis reactions (total solids being defined as soluble/dissolved and insoluble/undissolved solids). This large volume of water undesirably causes a dramatic increase in the volume of liquid being fed to the enzymatic hydrolysis reactor vessel, thereby making consistent control of the volume and temperature to the enzymatic hydrolysis reactor vessel more difficult.

The concentration of the pretreated biomass is indicated by the ratio of pretreated biomass to water. It is advantageous to maintain a high concentration pretreated biomass and a low concentration of water to ensure a high concentration of sugars in the product generated from the enzyme hydrolysis stage. Although adding water to cool pretreated biomass is effective, the addition of water undesirably tends to dilute the pretreated biomass and specifically the sugar solution produced by the enzymatic hydrolyzing of the pretreated biomass.

FIG. 1 shows a process flow diagram showing a conventional continuous system for treating biomass at a rate of fifty tonnes (dry basis) per hour. The biomass is pretreated in a pretreatment vessel 110. In this process the biomass is pretreated at elevated temperatures, such as above 100° C. and in an acidic environment. Other pretreatment processes, including, but not limited to, steam explosion or ammonium hydrolysis or lime hydrolysis, may be used. The pretreated biomass 111, may be discharged from the pretreatment vessel 110 at a rate of 166 cubic meters per hour ($m^3/h$) (for this example the a total solids content of twenty-five percent, 25%, was used), at a total solids content of twenty-five percent (25%) to fifty percent (50%) biomass solids (based on the biomass fed to the pretreatment reactor vessel), and at a temperature of at least 100° C. The total solids content for a biomass treatment process can be twenty-five percent (25%) to fifty percent (50%).

The pretreated biomass 111 is generally too acidic and too hot for enzymatic hydrolysis to occur because the conditions required for pretreatment of biomass are substantially different from the conditions favorable for enzyme hydrolysis. Enzyme hydrolysis usually occurs in an environment having a pH range of about 4 to 6.5 and at temperatures of, for example, about 50° C. to 55° C. Other temperature ranges may be used for enzyme hydrolysis. Yeast based enzyme reactions may occur in a range of, for example, about 28° C. to 40° C., thermophilic bacteria based enzymatic hydrolysis may occur at temperatures as high as about 80° C., and mesophilic bacteria based enzymatic hydrolysis may occur at temperatures between about 20° C. and about 45° C. A mixing stage 112, such as a mixing vessel, is used to adjust the pH and cool the pretreated biomass 111. An appropriate base 114 (a base is used in this example as the pretreatment conditions were acidic), such as ammonia, lime or other earth metal based hydroxide or carbonate, is added during the mixing stage 112 to adjust the pH of the pretreated biomass 111 to a level suitable for enzymatic hydrolysis.

A cooling liquid is added via conduit 116 in the mixing stage 112 to the pretreated biomass 111. The cooling liquid has typically been water, stillage or other suitable liquid from the mill. It has been proposed to use fully enzyme hydrolyzed biomass product 121. Typically after both pretreatment and enzymatic hydrolysis the biomass has a monomeric sugars yield of at least thirty percent (30%), and is discharged from a large enzymatic hydrolysis reactor vessel 118. The fully enzyme hydrolyzed biomass 121 may be split, with a portion via conduit 123 being pumped via pump 120 through a cooling stage 122 and to the mixing stage 112 via conduit 116.

In the mixing stage 112, batch mode mixing vessels are used to convert the pretreated biomass 111 to conditions suitable for enzymatic hydrolysis. Batch mode generally involves several smaller mixing vessels that feed a larger downstream vessel (not shown), such as a digester or other reactor vessel. Batch processing increases the volume needed in the mixing stage 112 vessels to accommodate the filling and emptying portions of each cycle for the mixing stage 112 vessel.

Enzymatic hydrolysis of pretreated biomass typically requires many hours to complete. The retention period in a large enzymatic hydrolysis reactor vessel 118 or assembly of vessels, for example, may be 24 to 72 hours or longer. The fully enzyme hydrolyzed biomass product 121 is discharged from the enzymatic hydrolysis reactor vessel(s) 118 and used as a manufactured monomeric sugar solution 119. Due to the long enzyme hydrolysis process periods, the volume of the large enzymatic hydrolysis reactor vessel(s) 118, e.g., tanks, are large for example could be as large as 37,000 $m^3$ or more. The high volume capacity, large size, required for the enzymatic hydrolysis vessels of the conventional continuous system results in limiting the biomass material to be processed.

A conventional large enzymatic hydrolysis reactor vessel 118 for enzyme hydrolysis tends to be much larger than a corresponding pretreatment vessel 110 used to pretreat the biomass. The pretreatment vessel 110 is much smaller because the pretreatment periods are typically much shorter than the process periods for enzyme hydrolysis.

As shown in FIG. 1 it is known to use, previously fully enzyme hydrolyzed biomass 121 as a cooling liquid to substitute in whole or part for water 130 to maintain a high concentration of pretreated biomass 111 in the mixing stage 112. The fully enzyme hydrolyzed biomass product 121 has been fully hydrolyzed (both from pretreatment processes and enzymatic hydrolysis) may be used as a manufactured monomeric sugar solution 119. The use of the fully enzyme hydrolyzed biomass product 121 as a cooling liquid avoids excessive dilution of adding cooling water 130. The use of fully enzyme hydrolyzed biomass product 121 as cooling liquid increases the needed volume of the large enzymatic hydrolysis reactor vessel(s) 118, e.g., tanks. Large enzymatic hydrolysis reactor vessel(s) 118 are needed to accommodate the long residence times, e.g., 24 to 72 hours or longer, needed for proper conversion of the pretreated biomass 111 from the pretreatment vessel 110, composed primarily of polymeric cellulose and hemi-cellulose to monomeric sugar solutions 119.

Other means for cooling pretreated biomass 111 (e.g., cooling gases or a cooling jacketed conveyor system) are known but may not be suitable for all process flow systems. Cooling gases, for example, often do not readily penetrate pretreated biomass 111 due to the fine particulate sizes of the pretreated biomass 111. Indirect heat exchangers are also often not suitable because the highly viscous pretreated biomass 111, e.g., a mud like consistency, does not readily flow through the passages of the heat exchanger. A cooling jacketed conveyor system between the pretreatment vessel 110 and the large enzymatic hydrolysis reactor vessels 118 may be used to cool pretreated biomass 111. However, the amount of heat transfer achieved in cooling jacketed conveyor systems may not be sufficient to cool the pretreated biomass 111 to the temperatures appropriate for enzymatic hydrolysis due to small area-to-volume ratios in the large diameter tube of the cooling jacketed conveyor systems and poor contact between the pretreated biomass 111 and the surfaces of the tube.

There is a long felt need for temperature and volume control of the pretreated biomass material to the reactor while reducing the need for the addition of fresh, cooling liquid (e.g., water) to the hot pretreated biomass from the appropriate pretreatment process.

SUMMARY OF EXAMPLE EMBODIMENTS

Except as otherwise expressly provided herein, the following rules of interpretation apply to this specification (i.e., written description, claims, abstract and/or drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, The terms "comprising," "having," "including," and "containing" are to be construed as open-ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range or within any sub ranges therebetween, unless otherwise clearly indicated herein. Each separate value within a recited range is incorporated into the specification or claims as if it were individually recited herein. Where a specific range of values is provided, it is understood that each intervening value, to the tenth or less of the unit of the lower limit unless the context clearly dictates otherwise, between the upper and lower limit of that range and any other stated or intervening value in that stated range or sub range thereof, is included therein. All smaller sub ranges are also included. The upper and lower limits of these smaller ranges are also included therein, subject to any specifically and expressly excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

The above and other features of the disclosed exemplary embodiments are achieved by providing an efficient apparatus, method and/or system to derive, produce or extract simple compounds from wood, pulp, fiber, lignocellulosic material, and the like (biomass), for use in other applications such as the production of fuel, including ethanol. In other aspects, the exemplary embodiments may be applied to decrease the apparent viscosity of viscous, cellulose-containing material to facilitate transport of the material to other processes. Further, the exemplary embodiments may be embodied to extract monomers of certain compounds from cellulose-containing materials, such as lignocellulosic materials (biomass). In addition, the exemplary embodiments may be applied to enzymatically hydrolyze pretreated biomass in order to produce monomeric sugars. Pretreatment of the biomass may employ one or more or a combination of processes including, but not limited to, acidic condition hydrolysis (with or without the addition of acid), steam explosion, ammonium hydrolysis or lime hydrolysis, etc.

Pretreatment using acidic condition hydrolysis of biomass may be with or without the addition of acids. Acidic condition hydrolysis without the addition of acid requires the addition of water and is frequently referred to as "autohydrolysis". Autohydrolysis requires a treatment atmosphere temperature of between about 150° C. (i.e., degrees Celsius) and 220° C. and a pH of about 1 to 6. In cases where the addition of acidic solutions is used to promote acidic condition hydrolysis, the temperature may be below 150° C. while the pH is 1 to 6.

Steam explosion of the biomass as a pretreatment step may occur at temperatures of, for example, about 170° C. to 230° C. for approximately two to five minutes (or longer), and at a gauge pressure of about eight (8) bar to 25.5 bar (800 kilopascals to 2,550 kilopascals). During steam explosion pretreatment, steam may be injected directly in the pretreatment vessel to provide heat energy, and one or more of steam, vapor and liquid water may be allowed to diffuse into the inner structure of the biomass. The steam and water vapor partially condense as liquid water in the capillary-like micro-porous structure of the inner structure of the biomass. The pressure of the biomass undergoing steam explosion pretreatment is reduced rapidly and dramatically, to one to two bars gauge, wherein zero bar gauge is at substantially atmospheric pressure. This large, rapid pressure drop results in steam explosion pretreatment of the biomass. The rapid pressure drop, e.g., "flashing", converts to steam the condensed liquid water in the cells of the biomass being pretreated. The conversion to steam of the water in the cells of the biomass causes a massive disruption, e.g., an "explosion", of the cells in the biomass. The disruption occurs because the volume occupied by the steam is much greater than the volume occupied by the water in the cells of the biomass. The massive disruption includes bursting individual cells of the biomass and rupturing the fibers along amorphous or crystalline cellulose, such as between the cylindrical tubes and fibers of the cellulosic structure of the biomass.

Another pretreatment process for the biomass may involve the use of liquid ammonia, lime, etc. as pretreatment agents. Use of these chemicals to pretreat the biomass may allow for improved efficiency of the subsequent enzymatic hydrolysis steps.

The example embodiments may involve recirculation of liquefaction material from one or more of the first enzymatic hydrolysis reactor vessel(s) output, which if necessary, has been cooled after discharge from the one or more first enzymatic hydrolysis reactor vessel(s) to produce a cool liquefaction material, to the hot pretreated biomass after, prior to, or in connection with, the direct addition of cooling liquid (such as cold water) and/or pH controlling (typically alkali, but in some circumstances could be acidic) material prior to the addition of one or more enzymes, optionally the enzymes are in a solution, to a pretreated biomass. It is important to provide the environment for enzyme hydrolysis where pH control in maintained, typically within a range of about 4 to 6.5. This pH control may be achieved by the addition of pH controlling material, in some cases alkali material may be added to achieve and control the pH, other cases may require acidic material to be added, and in still other cases there may not be a need to add any pH controlling material.

Liquefaction material, as defined for this application, is formed when the biomass becomes a fluid from at least partial enzyme hydrolysis. As used herein, enzymatic hydrolysis process steps are not limited to the use of enzymes, but may include the use of other catalysts such as yeast, thermophilic bacteria, mesophilic bacteria, or other biological catalyst. According to this example embodiment the liquefaction material is produced after partial enzyme hydrolysis. The liquefaction material suitable for recirculation as a cooling liquid upstream of the addition of fresh or new enzymes not previously in the process, (fresh or new enzymes not previously in the process is referred to as enzyme solution) and contains enzymes present in the first enzymatic hydrolysis reactor vessel(s) (recycle enzymes), has a conversion of cellulose to sugar or glucose (this conversion of cellulose to sugar or glucose is referred to herein as "hydrolysis") of less than about 30 percent, could be less than about 20 percent or even less than about 15 percent and an apparent viscosity of about 5,000 mPa·s or less, such as less than about 3,000 mPa·s, or less than about 2,000 mPa·s, or less than about 1,000 mPa·s or even less than about 800 mPa·s. Apparent viscosity being defined as the value obtained by applying the appropriate instrumental equations used by a skilled artisan in obtaining the viscosity of a Newtonian fluid to viscometer measurements of a non-Newtonian fluid. Because the liquefaction material of this application is a non-Newtonian fluid, the experimental parameters of the viscometer model, spindle and speed all have an effect on the measurement of the viscosity of the liquefaction material and result in viscosity being reported as "apparent viscosity". Apparent viscosity measurements may be obtained by using, without limitation, the well accepted Brookfield Viscometer with a cylindrical spindle, specifically the LV DV-II+ having 4 spindles and capable of operating at a speed of 0.1 to 200 revolutions per minute (rpm). Measurements of apparent viscosity obtained for purposes described herein using the specified equipment were obtained at a speed of 20 rpm. In this example embodiment, liquefaction material for recirculation as cooling material, the conversion of cellulose to sugar may be less than about thirty percent (30%) and the desired apparent viscosity may be less than about 5,000 mPa·s occurring while having a reaction/retention time of less than about six (6) hours in an at least first enzymatic hydrolysis reactor vessel.

The use of the liquefaction material from the discharge of, or after, the at least first enzymatic hydrolysis reactor vessel and the liquefaction material has been cooled to between about 20° C. and 50° C. provides a cool liquefaction material that is suitable for recirculation to provide at least some cooling liquid (reducing or eliminating the conventional need for the addition of cold water) for the hot pretreated biomass and by its use allows for the total solids content of the system to be maintained. By recirculating the cooled liquefaction material as at least a portion of a coolant for the pretreated biomass, the amount of required cooling water (fresh water, or water from another location within the process) is reduced. As a result, there is no need to increase the size of the at least first enzymatic hydrolysis reactor vessel over what would be required for the use of water alone. An advantage of a system where cool liquefaction material is used as at least a portion of the cooling liquid for the hot pretreated biomass is a reduced size/volume of the subsequent (second or further) enzymatic hydrolysis reactor vessel(s). In the system with recirculation of liquefaction material, the volume of flow from the first enzymatic hydrolysis reactor vessel to subsequent vessels is reduced by the volume of the recirculated cool liquefaction material. As a result of the reduced addition of water for cooling, the final sugar concentration yield is also increased, thereby reducing downstream processing costs in areas such as fermentation and distillation. The fully enzyme hydrolyzed biomass product discharged from subsequent or further enzymatic hydrolysis reactor vessels is not recirculated as cooling liquid; rather it is available for further processing or as a final product.

The material produced as a result of pretreatment of biomass (pretreated biomass) is typically at a temperature of about 100° C. Prior to the addition of the enzymes, the pretreated biomass temperature must be reduced to between about 30° C. and 80° C., about 40° C. to 60° C., about 45° C. to 50° C. in order to establish a suitable environment for the enzymes to be activated and react with the pretreated biomass. This example embodiment uses rapid enzymatic hydrolysis to obtain a liquefaction material in a short period of time of less than about six hours, less than about four hours, less than about three hours, less than about one hour. Not all pretreatment methods are conducive to use with the rapid enzymatic hydrolysis liquefaction process of this exemplary embodiment, therefore care must be taken in selecting the pretreatment process or processes. It may also be necessary to adjust (either reduce or increase) the solids concentration as well as adjust the pH of the pretreated biomass prior to introduction to the rapid enzymatic hydrolysis process of the example embodiments.

Enzymatic hydrolysis is used to produce monomeric sugars from pretreated biomass. Typically the conditions of the pretreated biomass to promote the desired enzymatic reactions are a temperature in the range of about 40° to 60° C. and a pH of about 4 to 6.5. The enzymatic hydrolysis reaction is endothermic, and may result in a slight cooling of the cooled and pH controlled pretreated biomass as the cooled and pH controlled pretreated biomass moves through the at least first enzymatic hydrolysis reactor vessel(s). A portion of the liquefaction material discharged from the at least first enzymatic hydrolysis reactor(s) vessel is removed, cooled and recirculated to the hot pretreated biomass typically at the point or downstream of the addition of the pH controlling material, and if needed additional cooling liquid such as water, (although the recirculated cool liquefaction material could be added with the pH controlling material or even after the addition of pH controlling material) and upstream of the addition of the enzyme solution. Prior to being added as a cooling liquid, the liquefaction material to be recirculated may be cooled using an indirect (or direct) heat exchanger to lower the temperature of the recirculated liquefaction material to the range of about 20° C. to 40° C. using fresh cold water, or stillage, or recirculated process liquid from the mill as cooling liquid to produce cool liquefaction material. The cooled recirculated cool liquefaction material is at least about 5° C. lower, at least about 10° C. lower, at least about 15° C. lower, at least about 20° C. lower than the stream entering the at least first enzymatic hydrolysis reactor vessel. The use of cool liquefaction material to replace at least partially water or recirculated process liquid from the mill, while ensuring proper temperature of the stream to the at least first enzymatic hydrolysis reactor vessel(s), also provides for obtaining a higher solids concentration of the stream entering the at least first enzymatic hydrolysis reactor vessel(s) compared if only water or recirculated process liquid from the mill were used. The high total solids content of the stream to the at least first enzymatic hydrolysis reactor vessel(s) results in higher glucose yield and concentration.

The recirculated cool liquefaction material may be introduced after the addition of pH controlling (typically alkaline but in some circumstances could be acidic) material, but may be introduced with or even prior to the pH controlling material should the pH of pretreated biomass be in the range necessary to avoid enzyme denaturation, but upstream of the addition of enzymes. In some cases, it may be desirable to introduce additional cooling liquid (such as cold water) along with the recirculated cool liquefaction material or the pH controlling material.

Enzymatic hydrolysis of lignocellulosic materials is challenging, especially with respect to the interactions between the enzymes and the lignocellulosic materials (and its derivatives), and due to the physical characteristics of the pretreated lignocellulosic particles or fibers, the monomeric/oligomeric mixture, e.g., slurry, and the rheological features thereof of the lignocellulosic material. There is a long felt need to reduce the overall amount of cooling liquid required, especially the amount of cold water required, by the introduction of recirculated enzymatic hydrolysis reactor discharge material into the hot steam exploded lignocellulosic material prior to enzyme addition.

In many industrial processes where biomass is converted to sugars involving steps of pretreatment and enzymatic hydrolysis, enzymatic hydrolysis may be undertaken in at least one step for a duration of about 96 hours, about 48 hours, or about 24 hours. An example embodiment requires enzymatic hydrolysis in at least one step, wherein the at least one step produces a rapid enzymatic hydrolysis liquefaction material, suitable for recirculation as pretreated biomass coolant material, in a period of about 0.5 to 6 hours and all—subranges therebetween to produce a liquefaction material. Enzymatic hydrolysis continues after the liquefaction material is produced.

The recirculation of cool liquefaction material according to this exemplary embodiment reduces the need for water addition as a coolant while allowing a higher solids concentration to be available for enzymatic hydrolysis after the initial rapid enzymatic hydrolysis phase which produces the liquefaction material has been completed. It has been found that recirculating at least some of the liquefaction material, after cooling, as at least some of the cooling liquid for the pretreated biomass increases the yield of glucose at the 72 hour enzymatic hydrolysis point by at least one percent (1%) over conventional systems where only water is used as the pretreated biomass coolant. This yield increase is dependent upon the pretreatment process used and yield increases of at least five percent (5%) over conventional processes have been achieved.

An apparatus, system (including a process flow system) and method have been conceived to cool and pH control pretreated biomass before entering an at least first enzymatic hydrolysis reactor vessel using liquefaction material extracted from the at least first enzymatic hydrolysis reactor vessel before further processing of the liquefaction material. The liquefaction material is cooled and mixed with the pretreated biomass. The liquefaction material may be extracted as it flows from a first enzymatic hydrolysis reactor vessel and before the material flows to subsequent, a second, or more, enzymatic hydrolysis reactor vessel(s).

The liquefaction material is substantially liquefied, even though the biomass has been enzymatically hydrolyzed for a relatively short period, such as about 0.5 to 6 hours (less than about six hours, less than about five hours, less than about four hours, less than about three hours, less than about two hours, less than about one hour). The liquefaction material has low apparent viscosity that may be similar to the apparent viscosity of biomass that has been fully enzyme hydrolyzed. For purposes of this application, fully enzyme hydrolyzed biomass has a sugar yield of greater than 30% as opposed to the liquefaction material sugar yield of less than 30%. The lower apparent viscosity liquefaction material may be pumped through a cooling device, such as an indirect heat exchanger, to produce cool liquefaction material and into the mixing stage. The mixing stage may be a continuous mixing device. The total solids content (dissolved plus undissolved solids) of the cooled and pH controlled pretreated biomass after the mixing device may be greater than about 30 percent, greater than about 25 percent, greater than about 20 percent, greater than about 15 percent, greater than about 10 percent of the total of mass flowing through the transfer system after the mixer. The process of pretreating and enzymatically hydrolyzing the biomass to form liquefaction material may be a continuous process rather than a batch or fed-batch process. Following the liquefaction material production, the subsequent or further enzymatic hydrolysis process may be continuous or batch.

It is also been identified that the use of multiple types of enzymes to comprise the enzyme solutions (fresh enzymes or enzymes not previously in the process) at different locations within the process is advantageous. For example, endoglucanases enzymes (enzymes that attack the center of the chain and break the chain into smaller polymeric or oligomeric fractions) may be useful to add prior to the first enzymatic hydrolysis reactor vessel. Following the first enzymatic hydrolysis reactor vessel, such as during further enzymatic hydrolysis, it may be advantageous to add exoglucanses enzymes (enzymes that attack the ends of the chain and break the chain to produce monomeric fractions) to continue the enzymatic hydrolysis. While introducing endoglucanases enzymes at one location and exoglucanases enzyme at a different location may be desired, having either or both types of enzymes in the recirculated cooling stream may occur, as both may be added prior to the at least first enzymatic hydrolysis reactor vessel.

A method has been conceived comprising: performing a pretreatment step on a biomass to produce a pretreated biomass; controlling the pH of the pretreated biomass to between about 4 to 6.5 (or about 4.5 to 6.5), controlling the pH of the pretreated biomass to between about 4 to 6.5 (or about 4.5 to 6.5) may require mixing the pretreated biomass with pH controlling material (typically an alkali-based compound, but in some circumstances may be an acidic compound, and in other circumstances no pH controlling material is added) until an average pH of the pretreated biomass is between from about 4 to about 6.5 or about 4.5 to 6.5 hours; adding at least recirculated cool liquefaction material, wherein the recirculated cool liquefaction material is only partially enzymatically hydrolyzed and produced in an at least first vessel, to the pretreated biomass to achieve an average temperature of the pretreated biomass of between about 40° C. to about 60° C. thereby producing a cooled and pH controlled pretreated biomass having a total solids concentration (wt % of the weight of total solids as compared to total weight of the cooled and pH controlled pretreated biomass) of between from about 10% to about 35%; transferring the cooled and pH controlled pretreated biomass to at least a first vessel; adding at least a first portion of an enzyme solution to the cooled and pH controlled pretreated biomass at the beginning of the transfer, or at the middle of the transfer or at the end of the transfer or any combination thereof to the at least first vessel to mix and transition the cooled and pH controlled pretreated biomass from a higher apparent viscosity to a lower apparent viscosity to create a substantially liquid material, wherein the temperature of the cooled and pH controlled pretreated biomass is kept at a temperature of from about 40° C. to 60° C., or about 45° C. to 55° C. from just prior to the addition of the at least first portion of the enzyme solution until exit from the at least first vessel.

In another embodiment, a method has been conceived comprising: performing a pretreatment step on a biomass to produce a pretreated biomass; controlling the pH of the pretreated biomass to between about 4 to 6.5 (or about 4.5 to 6.5), controlling the pH of the pretreated biomass to between about 4 to 6.5 (or about 4.5 to 6.5) may require mixing the pretreated biomass with pH controlling material (typically an alkali-based compound, but in some circumstances could be an acidic compound, and in some circumstances no pH controlling material is added) until an average pH of the pretreated biomass is from about 4 to 6.5 (or about 4.5 to 6.5), adding recirculated cool liquefaction material produced in an at least first vessel to the pretreated biomass to achieve an average temperature of the pretreated biomass is from about 40° C. to about 60° C. thereby producing a cooled and pH controlled biomass having a total solids concentration (wt % of weight of total solids as compared to total weight of the cooled and pH controlled pretreated biomass) of from about 10 to 35%; transferring the cooled and pH controlled pretreated biomass to at least a first vessel; adding at least a first portion of an enzyme solution to the cooled and pH controlled pretreated biomass to at least a first vessel wherein the at least first vessel allows to mix and transition the cooled and pH controlled pretreated biomass from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C. from just prior to the addition of the at least first portion of the enzyme solution until exit from the at least first vessel.

In yet another embodiment, adding at least a first portion of an enzyme solution to the cooled and pH controlled pretreated biomass at the beginning of the transfer, or at the middle of the transfer or at the end of the transfer or any combination thereof to at least a first vessel to mix and transition the cooled and pH controlled pretreated biomass from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C. from just prior to the addition of the at least first portion of the enzyme solution until exit from the at least first vessel.

A further embodiment may transfer the cooled and pH controlled pretreated biomass to a mixer via a positive displacement pump; mixing the cooled and pH controlled pretreated biomass in the mixer at a speed of from about 400 to 4,000 rpm, for about 0.05 to 200 seconds, wherein a first portion of an enzyme solution is added during said mixing; transferring the cooled and pH controlled pretreated biomass to at least a first enzymatic hydrolysis reactor vessel, wherein a second portion of the enzyme solution may be added, to transition the material from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C. from just prior to the addition of the first portion of the enzyme solution until exit from the at least first enzymatic hydrolysis reactor vessel.

In still another embodiment adding at least a first portion of the enzyme solution to the cooled and pH controlled pretreated biomass at the beginning of the transfer, or at the middle of the transfer or at the end of the transfer or any combination thereof to at least a first vessel wherein the first vessel is a mixer at a speed of from about 400 to 4,000 rpm, for about 0.05 to 200 seconds; transferring the cooled and pH controlled pretreated material from the first vessel to a second vessel, the second vessel being an at least first enzymatic hydrolysis reactor vessel, wherein a second portion of the enzyme solution may be added, to transition the material from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C. from just prior to the addition of the first portion of the enzyme solution until exit the first enzymatic hydrolysis reactor vessel.

One other embodiment includes adding at least a first portion of the enzyme solution to the cooled and pH controlled pretreated biomass at the beginning of the transfer, or at the middle of the transfer or at the end of the transfer or any combination thereof to at least a first vessel wherein the first vessel is a mixer at a speed of from about 400 to 4,000 rpm, for about 0.05 to 200 seconds; wherein a second portion of the enzyme solution may be added to the mixer; transferring the cooled and pH controlled material from a first vessel (mixer) to a second vessel, the second vessel being an at least a first enzymatic hydrolysis reactor vessel to transition the material from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C.

from just prior to the addition of the first portion of the enzyme solution until the exit of the first enzymatic hydrolysis reactor vessel.

Additionally, another embodiment provides no addition of enzyme solution prior to the first vessel, the first vessel being a mixer, the enzyme solution may be added at the mixer, transferring from the mixer to a second vessel where the second vessel is an at least first enzymatic hydrolysis reactor vessel to mix and transition the cooled and pH controlled pretreated biomass from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C. from just prior to the addition of the enzyme solution until exit of the at least first enzymatic hydrolysis reactor vessel.

Yet another embodiment provides for no addition of enzyme solution prior to a first vessel, the first vessel being a mixer, adding at least a portion of the enzyme solution to the mixer; transferring from the mixer to a second vessel, the second vessel being an at least enzymatic hydrolysis first reactor vessel; adding at least a second portion of enzyme solution during transfer to or to the at least first enzymatic hydrolysis reactor vessel to mix and transition the cooled and pH controlled pretreated biomass from a higher apparent viscosity to a lower apparent viscosity to create a substantially liquid material, wherein the temperature of the cooled and pH controlled pretreated biomass is maintained at a temperature of from about 40° C. to 60° C., or about 45° C. to 55° C. from just prior to the addition of the enzyme solution until exit of the at least first enzymatic hydrolysis reactor vessel.

The transfer of the pretreated biomass to the at least first vessel may be accomplished using at least one conveyor, wherein the recirculated cool liquefaction material from the at least first enzymatic hydrolysis reactor vessel and the pH control material (typically an alkali-based compound, but is some circumstances could be an acidic compound, and in some circumstances no pH controlling material is added) is added to the at least one conveyor until an average pH of the pretreated biomass is from about 4 to 6.5 (or about 4.5 to 6.5), and an average temperature of the pretreated biomass is from about 40° C. to 60° C., and the cooled and pH controlled pretreated biomass has a total solids concentration (wt % of weight of total solids as compared to total weight of the cooled and pH controlled pretreated biomass) of from about 10 to 35%; adding a first portion of an enzyme solution to the cooled and pH controlled pretreated biomass in the at least one conveyor, wherein the enzyme is added to the conveyor from more than one location inside the at least one conveyor; transferring the cooled and pH controlled pretreated biomass to the first vessel.

The transfer of the pretreated biomass to the at least first vessel may also involve multiple (two or more) conveyors and the addition of the recirculated cool liquefaction material and pH controlling material (if needed) are added at the first conveyor and the enzyme solution may be added at any of the multiple conveyors prior to entering the at least first vessel.

Yet another embodiment allows for the addition of the enzyme solution at multiple locations within the multiple conveyors.

A further method includes a step of adding a first portion of an enzyme solution to the cooled and pH controlled pretreated biomass occurs in a second of the multiple conveyors, wherein the enzyme is added to the second of multiple conveyors from more than one location inside the second of multiple conveyors.

The at least one enzymatic hydrolysis reactor vessels may be continuous enzyme hydrolysis reactors to transition the material from a higher apparent viscosity to a lower apparent viscosity to create a substantially liquefaction material wherein the temperature of the cooled and pH controlled pretreated biomass is maintained at a temperature of from about 40° C. to 60° C., or about 45° C. to 50° C., from just prior to the addition of the first portion of the enzyme solution until the exit of the at least first enzymatic hydrolysis reactor vessel.

In some exemplary embodiments, enzymes may be added at a single location, only as the cooled and pH controlled pretreated biomass is transferred to a first vessel, the first vessel being a mixer and the transfer being via a positive displacement pump. This single addition of enzymes could be at any point where the recirculated cool liquefaction material is added prior to or with the addition of the pH controlling material (if needed) and with or without the addition of cold water along with the pH controlling material.

The mixer of at least some embodiments may be a fluidizing mixer. In at least some embodiments, the mixer has a retention time of less than about 200 seconds, less than 0.5 seconds and all points in between. The speed of the mixer, in at least some of the embodiments, is greater than about 400 revolutions per minute (rpm) and less than about 4,000 rpm.

Mixing may occur in the mixer of the mixing stage or first vessel as well as within the at least first enzymatic hydrolysis reactor vessel(s). The mixer of the mixing stage or first vessel may be a high shear mixer, while the mixing in the at least first enzymatic hydrolysis reactor vessel(s) may be from a slow moving mixer.

An additional method has been conceived to treat a biomass comprising: pretreating the biomass at a temperature of at least about 100° C.; cooling and controlling the pH of the pretreated biomass to a temperature no greater than about 80° C. or no greater than about 50° C. and a pH of between about 1 and 6, using a continuous flow of cool liquefaction material and a pH controlling material; a step of enzyme hydrolyzing the cooled pretreated biomass using at least one of an enzyme, yeast, thermophilic bacteria or mesophilic bacteria or other biological catalyst to create a liquefaction material; extracting and recirculating the continuous flow of the liquefaction material produced from the cooled pretreated biomass in the enzyme hydrolyzing step.

The enzyme hydrolyzing step may include enzymatically hydrolyzing the cooled pretreated biomass in a first enzymatic hydrolysis reactor vessel to produce a liquefaction material and thereafter in a second or multiple enzymatic hydrolysis reactor vessel(s), and the extraction of the continuous flow of the liquefaction material occurs between the first and second enzymatic hydrolysis reactor vessels or at the first enzymatic hydrolysis reactor vessel discharge.

In another example embodiment, a process flow system has been conceived comprising: a pretreating reactor vessel configured to pretreat biomass at a temperature of at least about 100° C.; a cooling device configured to cool a continuous flow of the pretreated biomass to a temperature no greater than about 80° C. or no greater than about 50° C., wherein the cooling device uses a continuous flow of cool liquefaction material; a pH control device configured to add pH controlling material to the pretreated biomass; a first enzyme hydrolyzing reactor vessel configured to enzyme hydrolyze the cooled pretreated biomass using at least one of an enzyme, yeast, thermophilic bacteria, mesophilic bacteria, or other biological catalyst to produce a liquefaction material; further or subsequent multiple enzyme hydrolyzing reactor vessel(s) configured to enzyme hydrolyze the liquefaction material produced in the first enzyme hydrolyzing reactor vessel using at least one of an enzyme, yeast, thermophilic bacteria, mesophilic bacteria or other biological catalyst, wherein the further enzymatic hydrolyzing reactor vessel(s) is coupled to receive at least a portion of the liquefaction material discharged from the first enzyme hydrolyzing reactor vessel, and a pump configured to pump a portion of the liquefaction material to the cooling device.

DETAILED DESCRIPTION OF DRAWINGS

DETAILED DESCRIPTION OF EXAMPLE EMBODIMENTS

The exemplary methods and processes described here may be applied to enzymatically hydrolyze pretreated biomass to, for example, produce monomeric sugars. These methods and processes may be used to derive, produce or extract simple compounds from including, but not limited to, wood, pulp, fiber, agricultural waste, recycled fibers and the like, for the production of fuel, including ethanol, and other applications. Similarly, the described methods and processes may be embodied to extract monomers of compounds in cellulose-containing materials, such as lignocellulosic materials (biomass). Enzyme hydrolysis may include, but is not limited to, the use of one or more of the following: enzymes, yeast, thermophilic bacteria, mesophilic bacteria, or other biological catalysts.

Figure 1:
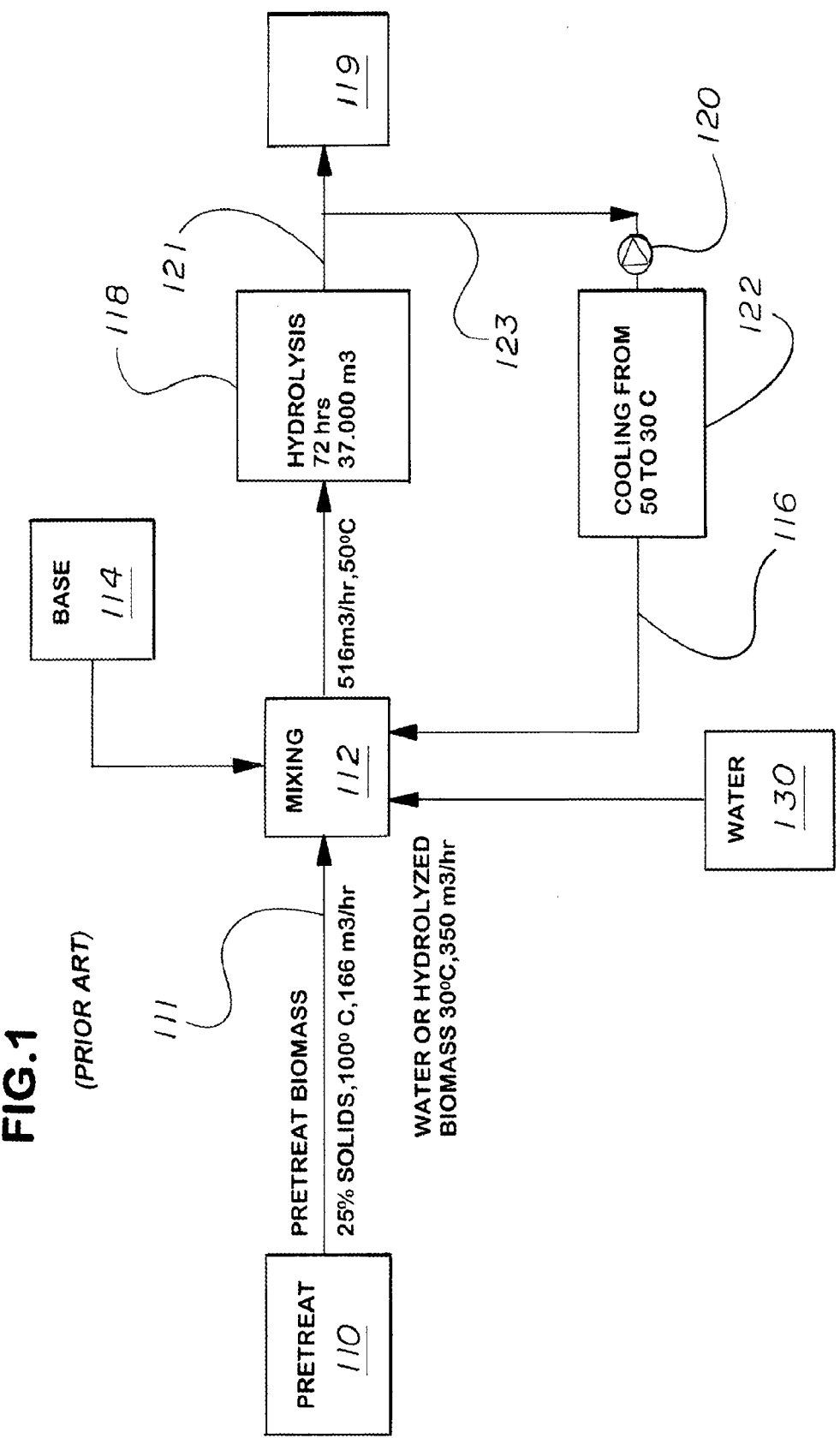
FIG. 1 depicts a process flow diagram of an exemplary prior art system for pretreating biomass, cooling the pretreated biomass and enzymatically hydrolyzing the cooled, pretreated biomass.

FIG. 1 shows a process flow diagram of a conventional continuous system for treating biomass at a rate of fifty tonnes (dry basis) per hour. The biomass is pretreated in a pretreatment vessel 110. In this process the biomass is pretreated at elevated temperatures, such as above 100° C. and in an acidic environment. Other pretreatment processes, including but not limited to steam explosion or ammonium hydrolysis or lime hydrolysis, may be used. The pretreated biomass 111, may be discharged from the pretreatment vessel 110 at a rate of 166 cubic meters per hour ($m^3/h$) (for this example the a total solids content of twenty-five percent, 25%, was used), at a total solids content of twenty-five percent (25%) to fifty percent (50%) biomass solids (based on the biomass fed to the pretreatment reactor vessel), and at a temperature of at least 100° C. The total solids content for a biomass treatment process can be twenty-five percent (25%) to fifty percent (50%).

The pretreated biomass 111 is generally too acidic and too hot to be processed by, or otherwise susceptible to the effects of, enzymatic hydrolysis. The conditions for pretreatment of biomass are substantially different from the conditions for enzyme hydrolysis. Enzyme hydrolysis usually occurs in an environment having a pH range of about 4 to 6.5 and at temperatures of, for example, about 50° C. to 55° C. Other temperature ranges may be used for enzyme hydrolysis. Yeast based enzyme reactions may occur in a range of, for example, about 28° C. to 40° C., thermophilic bacteria based enzymatic hydrolysis may occur at temperatures as high as about 80° C., and mesophilic bacteria based enzymatic hydrolysis may occur at temperatures between about 20° C. and about 45° C. A mixing stage 112, such as a mixing vessel, is used to increase the pH and cool the pretreated biomass 111. An appropriate base 114 (a base is used in this example as the pretreatment conditions were acidic), such as ammonia, lime or other earth metal based hydroxide or carbonate, is added during the mixing stage 112 to adjust the pH of the pretreated biomass 111 to a level suitable for enzymatic hydrolysis.

A cooling liquid is added via conduit 116 in the mixing stage 112 to the pretreated biomass 111. The cooling liquid has typically been water, stillage or other suitable liquid from the mill. It has been proposed to use fully enzyme hydrolyzed biomass product 121. Typically after both pretreatment and enzymatic hydrolysis the biomass has a monomeric sugars yield of at least thirty percent (30%), and is discharged from a large enzymatic hydrolysis reactor vessel 118. The fully enzyme hydrolyzed biomass 121 may be split, with a portion via conduit 123 being pumped via pump 120 through a cooling stage 122 and to the mixing stage 112 via conduit 116.

In the mixing stage 112, batch mode mixing vessels are used to convert the pretreated biomass 111 to conditions suitable for enzymatic hydrolysis. Batch mode generally involves several smaller mixing vessels that feed a larger downstream vessel (not shown), such as a digester or other reactor vessel. Batch processing increases the volume needed in the mixing stage 112 vessels to accommodate the filling and emptying portions of each cycle for the mixing stage 112 vessel.

Enzyme hydrolysis is a process that typically requires many hours to complete. The retention period in a large enzymatic hydrolysis reactor vessel 118 or assembly of vessels may be about 24 to 72 hours or longer. The fully enzyme hydrolyzed biomass product 121 is discharged from the enzymatic hydrolysis reactor vessel(s) 118 and used as a manufactured monomeric sugar solution 119. Due to the long enzyme hydrolysis process periods, the volume of the large enzymatic hydrolysis reactor vessel(s) 118, e.g., tanks, are large for example could be as large as about 37,000 m$^3$. The high volume capacity, large size, required for the enzymatic hydrolysis vessels of the conventional system could result in limiting the biomass material to be processed or in increased costs of the enzymatic hydrolysis system.

A conventional large volume enzymatic hydrolysis reactor vessel 118 for enzyme hydrolysis tends to be much larger than a corresponding pretreatment vessel 110 used to pretreat the biomass. The pretreatment vessel 110 is much smaller because the pretreatment periods are typically much shorter than the process periods for enzyme hydrolysis.

As shown in FIG. 1 it is known to use previously fully enzyme hydrolyzed biomass 121 as a cooling liquid to substitute in whole or part for water 130 to maintain a high concentration of pretreated biomass 111 in the mixing stage 112. The fully enzyme hydrolyzed biomass product 121 has been fully hydrolyzed (both from pretreatment processes and enzymatic hydrolysis) and may be used as a manufactured monomeric sugar solution 119. The use of the fully enzyme hydrolyzed biomass product 121 as a cooling liquid avoids excessive dilution of adding cooling water 130. The use of fully enzyme hydrolyzed biomass product 121 as cooling liquid increases the needed volume of the large enzymatic hydrolysis reactor vessel(s) 118, e.g., tanks. Large enzymatic hydrolysis reactor vessel(s) 118 are needed to accommodate the long residence times, e.g., 24 to 72 hours or longer, needed for proper conversion of the pretreated biomass 111 from the pretreatment vessel 110, composed primarily of polymeric cellulose and hemi-cellulose to monomeric sugar solutions 119.

Other means, for example cooling gases or a cooling jacketed conveyor system, for cooling pretreated biomass 111 are available but may not be suited for all process flow systems. Cooling gases often do not readily penetrate pretreated biomass 111 due to the fine particulate sizes of the pretreated biomass 111. Indirect heat exchangers are often not suitable because the highly viscous pretreated biomass 111, e.g., a mud like consistency, does not readily flow through the passages of the heat exchanger. A cooling jacketed conveyor system between the pretreatment vessel 110 and the large enzymatic hydrolysis reactor vessels 118 may be used to cool pretreated biomass 111. However, the amount of heat transfer achieved in cooling jacketed conveyor systems may not be sufficient to cool the pretreated biomass 111 to the temperatures appropriate for enzymatic hydrolysis due to small area-to-volume ratios in the large diameter tube of the cooling jacketed conveyor systems and poor contact between the pretreated biomass 111 and the surfaces of the tube. The poor heat transfer may thus result in the need for very large and expensive indirect cooling systems.

Figure 2:
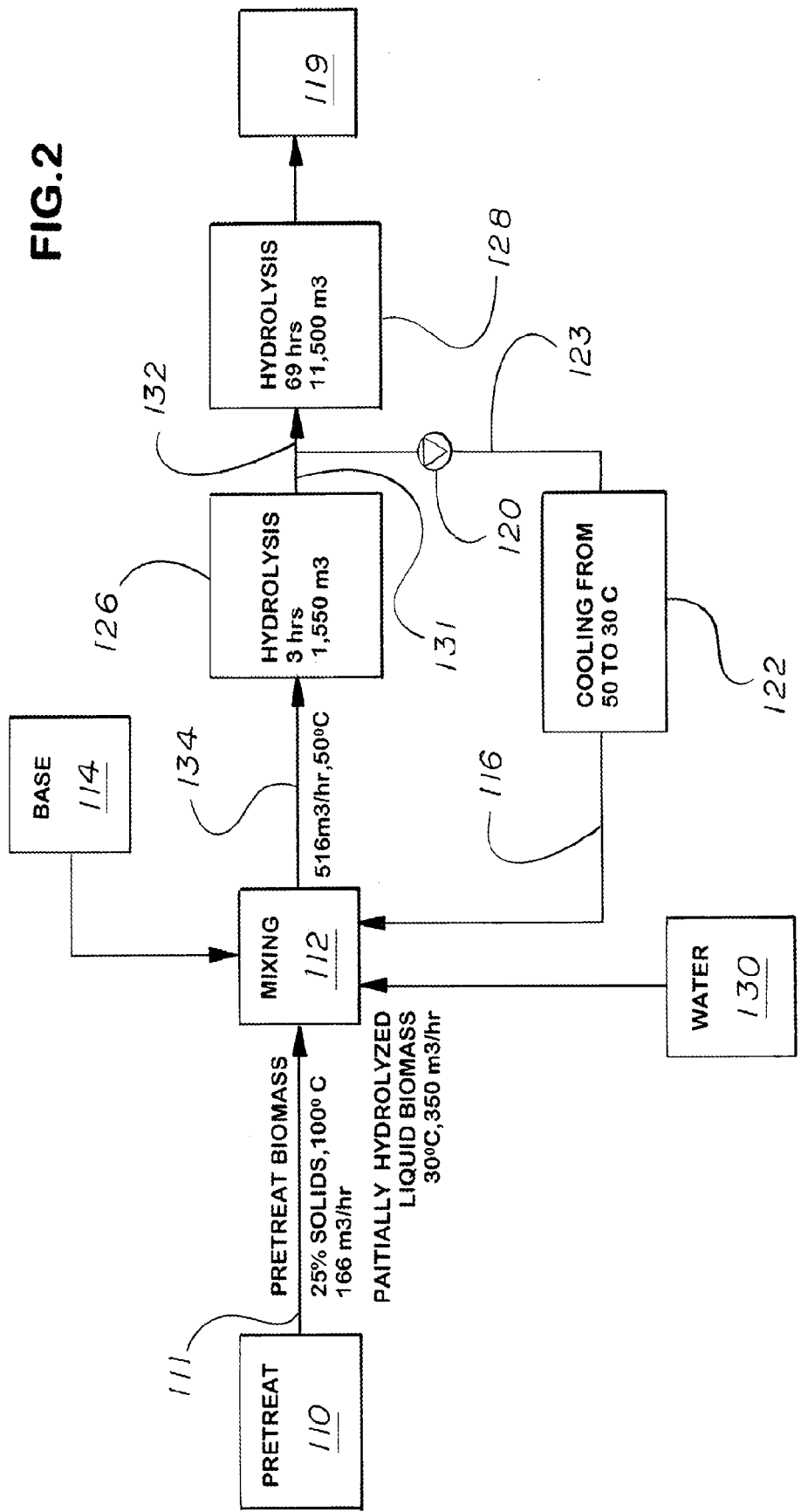
FIG. 2 depicts a process flow diagram of a novel system for pretreating biomass, cooling the pretreated biomass and enzymatically hydrolyzing the cooled, pretreated biomass.

FIG. 2 depicts a process flow diagram of a novel system for treating biomass at a rate of about fifty (50) tonnes (dry basis) per hour. The system is similar to that shown in FIG. 1 and common reference numerals are used to refer to common process structures and steps. The biomass is pretreated in a pretreatment vessel 110, such as at temperatures above about 100° C. and in an acidic environment. The pretreated biomass 111 may be discharged from the pretreatment vessel 110 at a rate of about 166 cubic meters per hour (m$^3$/h).

A mixing stage 112 may be a continuous flow mixing device, such as mixing tank or screw conveyor. An appropriate base 114, such as ammonia, lime or other earth metal based hydroxide or carbonate, is added during the mixing stage 112 to control, e.g., increase or decrease, the pH of the pretreated biomass to a level suitable for enzymatic hydrolysis.

A cooling liquid is added in the mixing stage 112 and into the pretreated biomass 111 via conduit 116. The cooling liquid is liquefaction material (partially enzyme hydrolyzed biomass material) 131 discharged from a first enzymatic hydrolysis reactor vessel 126. The liquefaction material 131 passes via conduit 123 and is pumped via pump 120 through a cooling stage 122 and to the mixing stage 112 via conduit 116. The cooling stage 122 may be an indirect cooling device such as a heat exchanger or cooling jacket around a transport conduit for the partially enzyme hydrolyzed biomass. The cooling stage may reduce the temperature of the liquefaction material to about 50° C. to 30° C., thereby producing a cool liquefaction material.

The first enzymatic hydrolysis reactor vessel 126 may be a relatively small vessel, such as having a volume of about 1,550 m$^3$, or a volume in a range of about 750 to 500 m$^3$. The vessel 126 may be conical with an upper inlet at a narrow end of the vessel. In an upstream (upper) region of the vessel, the mixing arms may be relatively short and relatively long in a downstream (lower) region of the vessel. The upper region of the first enzymatic hydrolysis reactor vessel 126 is suited to processing the high apparent viscosity pretreated biomass 111, which is often a fine particle solid-water mixture or very high apparent viscosity mud-like substance. During enzyme hydrolysis in the first enzymatic hydrolysis reactor vessel 126, solids in the pretreated biomass 111 are converted to a liquid which has a relatively low apparent viscosity. Due to the low apparent viscosity, the torque needed to move the long mixing arms in the lower region of the first enzymatic hydrolysis reactor vessel 126 may be substantially similar to the torque needed to move the short mixing arms through the more viscous cooled and pH controlled pretreated biomass 134 in the upper region of the first enzymatic hydrolysis reactor vessel 126.

The cooled and pH controlled pretreated biomass 134 may have a relatively short retention period, e.g., about 0.5 to 6.0 hours, in the first enzymatic hydrolysis reactor vessel 126. The retention time needed to partially convert the solids from cellulose to sugars in the cooled and pH controlled pretreated biomass 134 to liquefaction material 131 in the first enzymatic hydrolysis reactor vessel 126 may be less than about 6 hours and can be less than 3 hours or less than 2 hours. At end of the short retention time, e.g., between about 6 to 0.5 hours, enzymatic hydrolysis of the cooled and pH controlled pretreated biomass 134 is not complete, i.e. fully enzyme hydrolyzed biomass has not been produced.

The enzymatic hydrolysis process in the first enzymatic hydrolysis reactor vessel 126 lowers the apparent viscosity of the cooled and pH controlled pretreated biomass 134 due to the scission of the long chain polymers of the cooled and pH controlled pretreated biomass 134 into shorter molecules. Because it is substantially a liquid and has a low apparent viscosity (relative to the pretreated biomass), the liquefaction material 131 can be split, and at least a portion via conduit 123, and may be continuously pumped via pump 120 through the cooling stage 122 to the mixing stage 112 via conduit 116.

The mixing stage 112 may be a continuous process. In a continuous process, a continuous flow of liquefaction material 131 flows from the discharge of the first enzymatic hydrolysis reactor vessel 126, is pumped via pump 120 through the cooling stage 122, e.g., an indirect cooling device or conduit with cooling jackets (where a cool liquefaction material is produced), and flows into a mixing device, such as a screw conveyor and mixer, within the mixing stage 112. The rate at which a portion of the liquefaction material 131 flows through conduit 123 into the cooling stage 122 is regulated to control the temperature of the mixture of pretreated biomass 111 and cooled and pH controlled pretreated biomass 134 entering the upper inlet to the first enzymatic hydrolysis reactor vessel 126. In addition, base material 114 may be added to control, e.g., increase the pH of the mixture of pretreated biomass 111 and liquefaction material 131 and additional water 130 may be added for cooling.

The portion of liquefaction material 131 not diverted to cool the pretreated biomass 111 flows via conduit 132 to a second enzymatic hydrolysis reactor vessel(s) 128. Transfer of the portion of liquefaction material 131 to a second enzymatic hydrolysis reactor vessel(s) 128 may be via a pump (not shown). The second enzymatic hydrolysis reactor vessel(s) 128 may be a conventional tank, e.g., cylindrical vessels, and have a volume different (for example the second enzymatic hydrolysis reactor vessels(s) may require a volume of about 11,500 m$^3$) than the first enzymatic hydrolysis reactor vessel 126 (the first enzymatic hydrolysis reactor vessel 126 may have a volume of about 1,550 m$^3$). Because a portion of liquefaction material 131 is used to cool the pretreated biomass 111, the capacity required for the second enzymatic hydrolysis reactor vessel 128 need not be as large as large as the single enzymatic hydrolysis reactor vessel 118 of the conventional system of FIG. 1. The second enzymatic hydrolysis reactor vessel(s) 128 may operate in continuous or batch modes. The period to complete enzyme hydrolysis in the second enzymatic hydrolysis reactor vessel(s) 128 may be relatively long, such as about 21 to 69 hours or longer. While the combined period for enzymatic hydrolysis occurring in the first enzymatic hydrolysis reactor vessel 126 and the second enzymatic hydrolysis reactor vessel(s) 128 may be similar to a conventional enzymatic hydrolysis period in the process such as shown in FIG. 1, the total volume of the first enzymatic hydrolysis reactor vessel 126 and the second enzymatic hydrolysis reactor vessel 128 of the exemplary embodiment (FIG. 2) may be significantly less, about 13,050 m$^3$ rather than about 37,000 m$^3$ for the conventional system of FIG. 1. The reduction in total capacity for enzymatic hydrolysis between conventional (FIG. 1) systems and the exemplary embodiment (FIG. 2) system is significant and results in a large cost savings for equipment.

As previously discussed, the combined volume of the first and second enzymatic hydrolysis reactor vessels 126, 128 may be substantially less than the volume of an enzymatic hydrolysis reactor vessel such as shown in FIG. 1. By using liquefaction material 131 (partially enzyme hydrolyzed biomass) along with water 130 to cool and adjust the solids concentration of the pretreated biomass 111 and using a continuous process for mixing and enzymatic hydrolysis, the volumes needed in the mixing stage 112 and enzymatic hydrolysis reactor vessels 126, 128 shown in the process illustrated in FIG. 2 are substantially reduced as compared to the volumes needed for the processes shown in FIG. 1.

Figure 3:
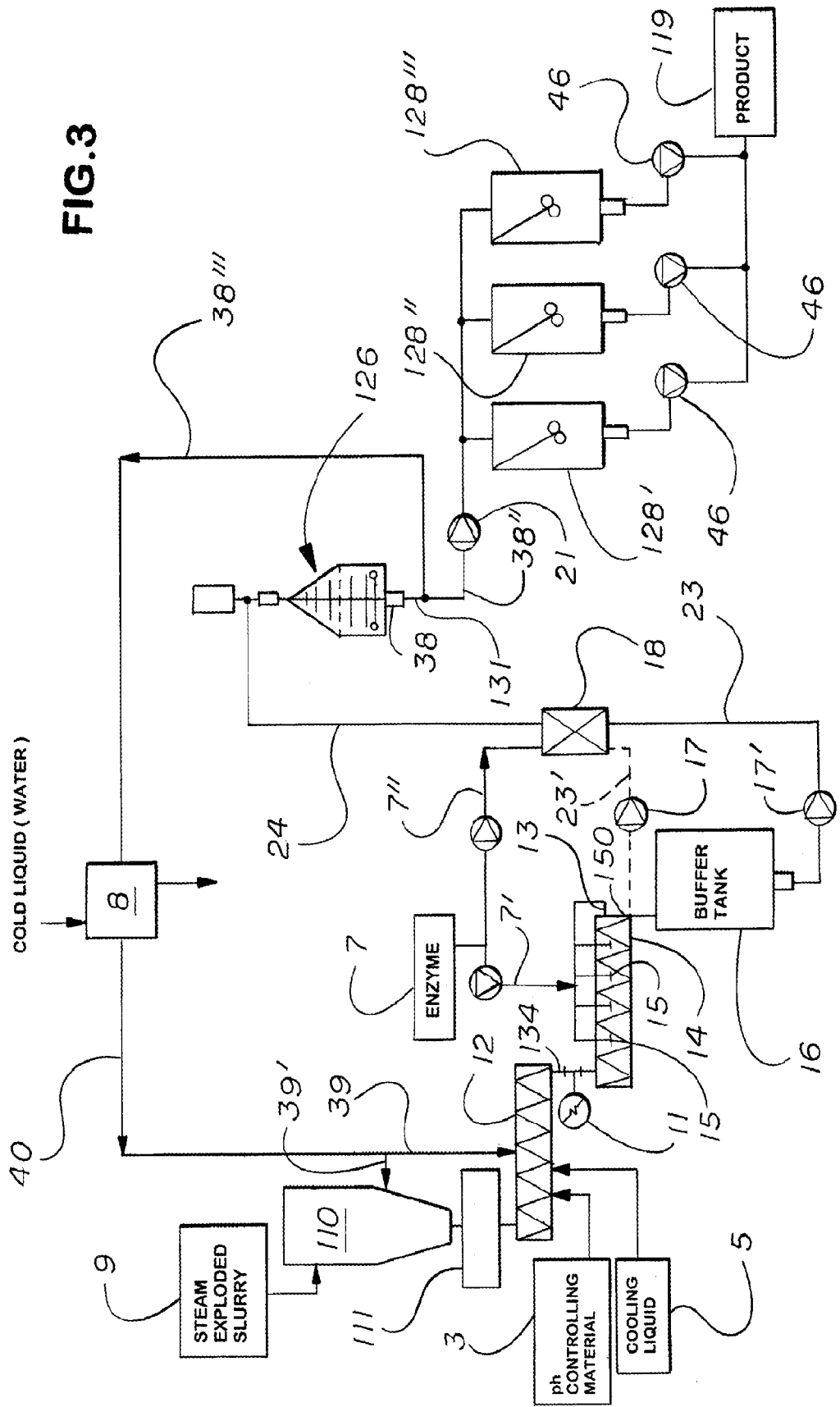
FIG. 3 depicts a process flow diagram of the overall process by which the lignocellulosic materials are mixed with one or more enzymes or enzyme-containing solutions in an enzymatic hydrolysis reaction in order to produce monomeric sugars or other useful by-products using recirculated liquefaction material for cooling.

In FIG. 3, common reference numerals are used to refer to common process structures and steps as shown in FIGS. 1 and 2, shows an exemplary embodiment for mixing an enzyme with pretreated biomass. Pretreated lignocellulosic biomass 9 enters a buffer tank 110 (buffer tank 110 may be a cyclone or other vessel), in some embodiments the pretreated lignocellulosic biomass 9 enters the buffer tank 110 as a slurry and exits the buffer tank 110 as pretreated biomass 111, in certain example embodiments, the pretreated biomass 111 is transferred from the buffer tank 110 to a first conveyor 12. The pretreated lignocellulosic biomass 9 may have an apparent viscosity of greater than about 10,000 mPa·s, or an apparent viscosity of greater than about 15,000 mPa·s, or, in other example embodiments an apparent viscosity of greater than about 20,000 mPa·s or even about 25,000 mPa·s. The pretreated lignocellulosic biomass 9 in the buffer tank 110 may be at a temperature of about 100° C. (within about 15° C. of 100° C.), may be 40% solids by weight and may have a pH of about 1 to 4. From the buffer tank 110, the pretreated biomass 111 is transferred to the first conveyor 12. The first conveyor 12 may be a screw, or more particularly, a "cooling and pH controlling screw." In this first conveyor 12, in certain examples, the temperature or pH of the pretreated biomass 111 may be altered, as described above, such that the conditions are made more ideal for the enzyme. In certain example embodiments, the temperature of the pretreated biomass 111 is lowered, and the pH is raised. Liquefaction material 131 exits the first enzymatic hydrolysis reactor vessel 126 discharge device 38 and may be split into a first liquefaction material portion 38''' to be recirculated to the buffer tank 110 and/or first conveyor 12 and a second liquefaction material portion 38'' sent to pump 21. The first liquefaction material portion 38''' is cooled in cooler 8 to produce a cooled first liquefaction material portion 40. The temperature of pretreated biomass 111 from the buffer tank 110 in first conveyor 12 can be reduced via the addition of recirculated liquefaction material 131, specifically cooled first liquefaction material portion 40. However, this is illustrative only, and may not always be the case depending on the pH or temperature of the mixture during or after pretreatment.

Liquefaction material 131 discharged from the first enzymatic hydrolysis reactor 126 is discharged via reactor discharge device 38 at a temperature of about 40° C. to 55° C. A portion of the liquefaction material 131 discharged through device 38, can be recirculated to the buffer tank 110 via conduit 39' and/or to first conveyor 12 via conduit 39. To cool the first liquefaction material portion 38''' being recirculated from the reactor discharge device 38, a cooler (such as an indirect heat exchanger or other suitable device) 8 may be used to reduce the temperature of the recirculating first liquefaction material portion 38''' to between about 20° C. to 40° C. using cold water or other suitable cooling liquid creating a cooled first liquefaction material portion 40.

In certain example embodiments, while in the first conveyor 12, pH controlling materials 3, such as an alkali compound or acidic compound if warranted, or temperature-changing materials (via conduit 39), such as recirculated cooled first liquefaction material portion 40 and/or cooling liquid 5 (such as cold water, stillage or process liquid from the mill), may be added to the pretreated biomass 111 in order to control the pH, or total solids consistency or temperature of the pretreated biomass 111 such that these values fall into the ranges necessary for enzymatic hydrolysis. A sensor 11, such as a temperature and/or pH sensor, may monitor the cooled and pH controlled pretreated biomass 134 discharged by the first conveyor 12 and provide data for controlling the pH and temperature of the pretreated biomass 111 fed into the first conveyor 12.

In certain examples, the at least a portion of the recirculated cooled first liquefaction material 40 can be added to the buffer tank 110 via conduit 39' and pH controlling materials 3 may be alkali-based compounds (or if necessary an acidic compound) with or without the additional recirculated cooled first liquefaction material 40 being added via conduit 39 to the pretreated biomass 111.

In certain examples, the recirculated cooled first liquefaction material 40 can be added to the buffer tank 110 via conduit 39' and pH controlling materials 3 may be alkali-based compounds (or if the situation requires an acidic compound) with the addition of cooling liquid 5, such as cold water, stillage or process stream from the mill, may be added to the pretreated biomass 111.

In other example embodiments, if the pH of the pretreated biomass 111 is too high, pH controlling materials 3 comprising acidic compounds may be added in order to control the pH of the pretreated biomass 111 such that these values fall into the above-described ranges. In further example embodiments, while in the first conveyor 12, the total solids concentration of the pretreated biomass 111 is reduced to about 10 to 30% by weight, or to about 15 to 30%, or to about 18 to 25%.

After the pH, or temperature, or the total solids concentration of the pretreated biomass 111 is altered via the addition of pH controlling materials 3 e.g., alkali compounds, and temperature changing materials via conduits 39' and/or 39 and/or, e.g., recirculated cooled first liquefaction material 40 and cooling liquid 5, in first conveyor 12 so as to fall within a more ideal or desired range for performance of the enzyme, the cooled and pH controlled pretreated biomass 134 may be transferred to a second conveyor 14 which may also be a screw conveyor. In this second conveyor 14, an enzyme solution first portion 7' of the enzyme solution 7 may be sprayed or otherwise combined with the cooled and pH controlled pretreated biomass 134 in the second conveyor 14. In some cases, the enzyme solution first portion 7' may be sprayed in the second conveyor 14 via spray nozzles 15 that are evenly distributed throughout the second conveyor 14. In other example embodiments, the enzyme solution first portion 7' may be added to the cooled and pH controlled pretreated biomass 134 via axial inlets 13 (which may be on both ends of the second conveyor 14), or inlets located in various irregularly spaced positions on the second conveyor 14.

Following the addition of the enzyme solution first portion 7' to the slurry 150, (the slurry having cooled and pH controlled pretreated biomass 134 and including the enzyme solution first portion 7') may be transferred to a vessel 16. In certain example embodiments, the slurry 150 will remain in vessel 16 until more slurry 150 is added to the vessel 16 for the remaining processing steps. The vessel 16 may be a buffer tank. In other example embodiments, the slurry 150 may be transferred directly from the second conveyor 14 to a mixer 18, rather than going to the vessel 16. In some embodiments, the mixer 18 may be a fluidizing mixer. In some instances, a positive displacement pump 17' may be used to transfer the slurry 150 to the mixer 18 via pipes 23 from vessel 16. The positive displacement pump 17' may be a medium consistency positive displacement pump. The positive displacement pump 17' may alternatively be in a pipe 23' extending directly from the second conveyor 14 to the mixer 18.

In certain example embodiments, when the slurry 150 is transferred to the mixer 18, the slurry 150 may have an apparent viscosity as low as about 2,000 mPa·s to 3,000 mPa·s.

The mixer 18 may be a medium consistency mixer. The enzyme solution second portion 7" may be added to mixer 18 with the slurry 150. Alternatively, once the slurry 150 is transferred to mixer 18, the slurry 150 may be mixed, and thereafter enzyme solution second portion 7" may be added to the slurry 150. In some cases, the enzyme solution second portion 7" may be added prior to mixing the slurry 150 and enzyme solution second portion 7". In other example embodiments, the enzyme solution second portion 7" may be added simultaneously to, or subsequent to, the start of the mixing. In further example embodiments, enzyme solution second portion 7" may be added to the mixer 18 at the same time that the slurry 150 is added to mixer 18 such that both the slurry 150 and enzyme solution second portion 7" are both present prior to the start of mixing.

In an exemplary embodiment, the enzyme solution second portion 7" and the slurry 150 are added to the mixer 18 substantially simultaneously, while the mixer 18 is operating at rotational speeds such as speeds in ranges of about 200 to 6,000 rpm (revolutions per minute), about 300 to 5,000 rpm, and about 400 to 4,000 rpm. The slurry 150 and the enzyme solution second portion 7" may be mixed for certain predetermined periods such as periods in ranges of about 0.05 to 500 seconds, about 0.1 to 300 seconds, and about 0.1 to 100 seconds. Mixing of the slurry 150 and enzyme solution second portion 7" in the mixer 18 in this manner and at the above-discussed speeds may advantageously result in a faster digestion by the enzymes of the lignocellulosic particles and polymeric sugars in slurry 150, without significantly degrading or denaturing the enzymes from the enzyme solution 7.

After both enzyme solution first portion 7' and enzyme solution second portion 7" have been mixed into the slurry 150, the slurry 150 may then be transferred e.g., pumped, to another vessel, a first enzymatic hydrolysis reactor vessel 126. The first enzymatic hydrolysis reactor vessel 126 may be a high consistency reactor or mixer. The first enzymatic hydrolysis reactor vessel 126 may permit a smoother transition from a very viscous material to a less viscous material, or even a liquid, in certain example embodiments.

In some embodiments, mixer 18 and first enzymatic hydrolysis reactor vessel 126 may be a single piece of equipment (such as a mixer/reactor not shown) allowing the functions of mixing and enzymatic hydrolysis to provide a liquefaction material be performed in a single piece of equipment.

It is also possible to have the transfer, cooling and pH controlling functions to occur in a single piece of transfer equipment, not limited to a screw conveyor or multiple screw conveyors, prior to the addition of any enzyme solution 7 to the cooled and pH controlled pretreated biomass 134. In some embodiments, the addition of enzyme solution 7 may be made only during the transfer of the cooled and pH controlled pretreated biomass 134, prior to the mixer 18 and first enzymatic hydrolysis reactor vessel 126 or the combined single mixer/reactor equipment. In yet other embodiments, the addition of enzyme solution may be only at the mixer 18 or only at the first enzymatic hydrolysis reactor vessel 126 or at the combined single mixer/reactor equipment.

A recirculation loop is produced using the liquefaction material 131 discharged through reactor discharge device 38. Liquefaction material 131 may be divided into at least two portions, one 38" (second liquefaction material portion 38") sent to liquefaction material pump 21 for further handing and another portion 38''' (first liquefaction material portion 38'''') sent to a cooler 8 where it is cooled and recirculated to pretreatment vessel 110 and/or first conveyor 12 or other suitable location prior to injection of enzyme solution 7 and pH controlling material 3 as required.

As shown in FIG. 3, after the slurry 150 has become liquefaction material 131 to be discharged through reactor discharge device 38 in the first enzymatic hydrolysis reactor vessel 126, a liquefaction material pump 21 may be used to transfer the second liquefaction material portion 38" to at least one second enzymatic hydrolysis reactor vessel 128' (128", 128''') where further liquefaction or further enzymatic hydrolysis may take place, in certain example embodiments. Liquefaction material pump 21 used to transfer the second liquefaction material portion 38" to second enzymatic hydrolysis reactor vessels 128', 128" 128''' may be a centrifugal or positive displacement pump in certain example embodiments. In further example embodiments, the at least one second enzymatic hydrolysis reactor vessel 128' (128", 128''') may be a single second enzymatic hydrolysis reactor vessel. In some cases, substantially complete enzymatic hydrolysis may take place in one or more second enzymatic hydrolysis reactor vessels 128', 128", 128''', each with rotating mixing devices. The product 119 discharged from the second enzymatic hydrolysis reactor vessels 128', 128", 128''' may be a stream of the fully enzymatic hydrolyzed biomass.

In certain example embodiments, products 119 of the enzymatic hydrolysis process may include sugars, such as monomeric sugars and may be pumped by product pumps 46 to be used in a wide variety of fields or uses. The product pumps 46 may be positive displacement pumps. The products 119 may be used to produce ethanol, or any other value-added chemical.

Figure 4:
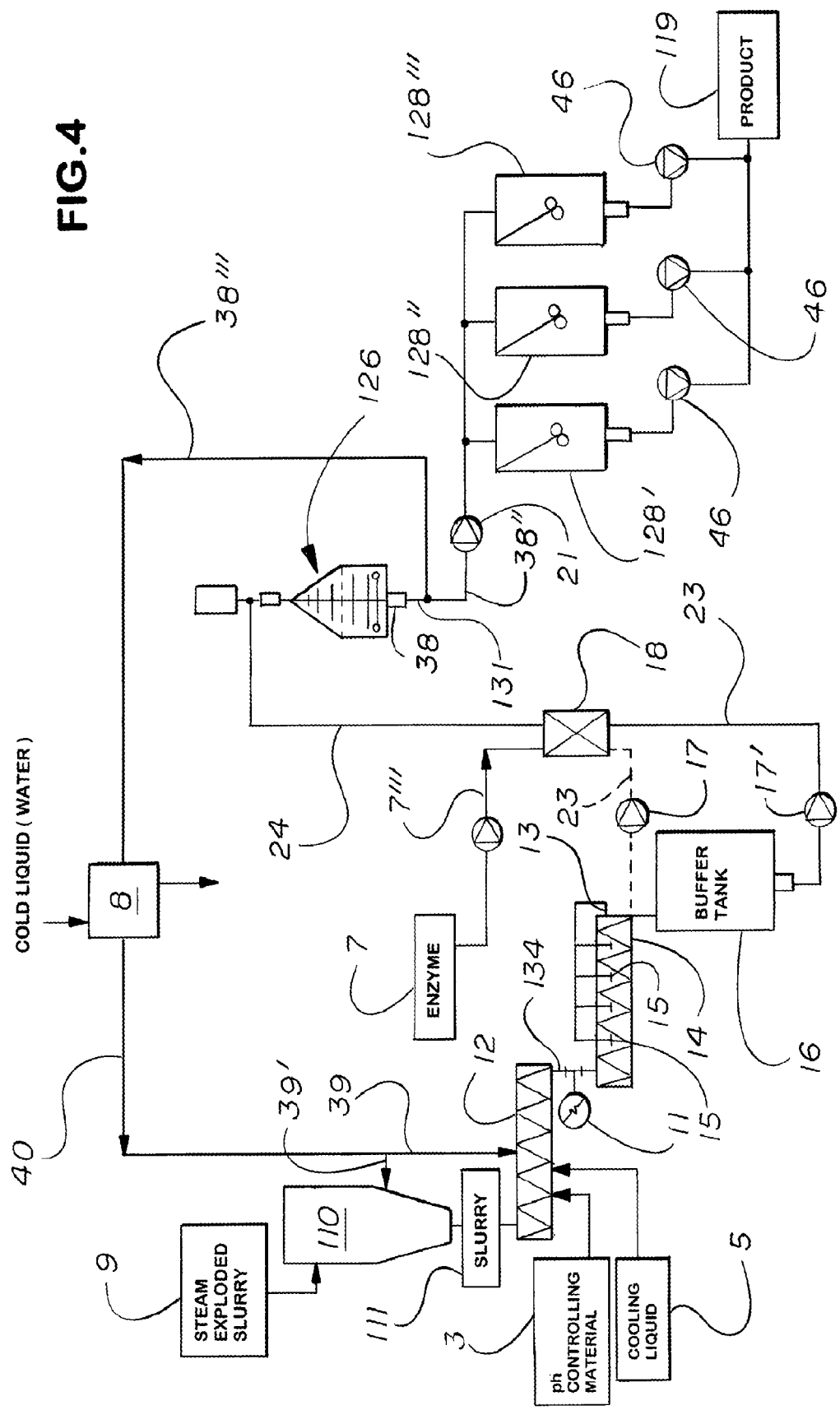
FIG. 4 depicts a process flow diagram of the overall process by which the lignocellulosic materials are mixed with one or more enzymes or enzyme-containing solutions using a single enzymatic addition in an enzymatic hydrolysis reaction in order to produce monomeric sugars or other useful by-products using recirculated liquefaction material for cooling.

FIG. 4 (equipment and streams common to FIGS. 1 to 3 use the same reference numbers) shows an alternative embodiment where there is a single addition of enzyme solution 7 via conduit 7''' through mixer 18, no addition of enzyme solution 7 is made at the second conveyor 14. In such instances a second conveyor 14 may not be needed. The enzyme solution portion 7 may be added to mixer 18 with the cooled and pH controlled pretreated biomass 134. Alternatively, once the cooled and pH controlled pretreated biomass 134 is transferred to mixer 18, the cooled and pH controlled pretreated biomass 134 may be mixed, and thereafter enzyme solution 7 may be added to the cooled and pH controlled pretreated biomass 134. In some cases, the enzyme solution 7 may be added prior to mixing the cooled and pH controlled pretreated biomass 134 and enzyme solution 7. In other example embodiments, the enzyme solution 7 may be added simultaneously to, or subsequent to, the start of the mixing. In further example embodiments, enzyme solution 7 may be added to the mixer 18 at the same time the cooled and pH controlled pretreated biomass 134 is added to mixer 18 such that both present in mixer 18 prior to the start of mixing.

Figure 5:
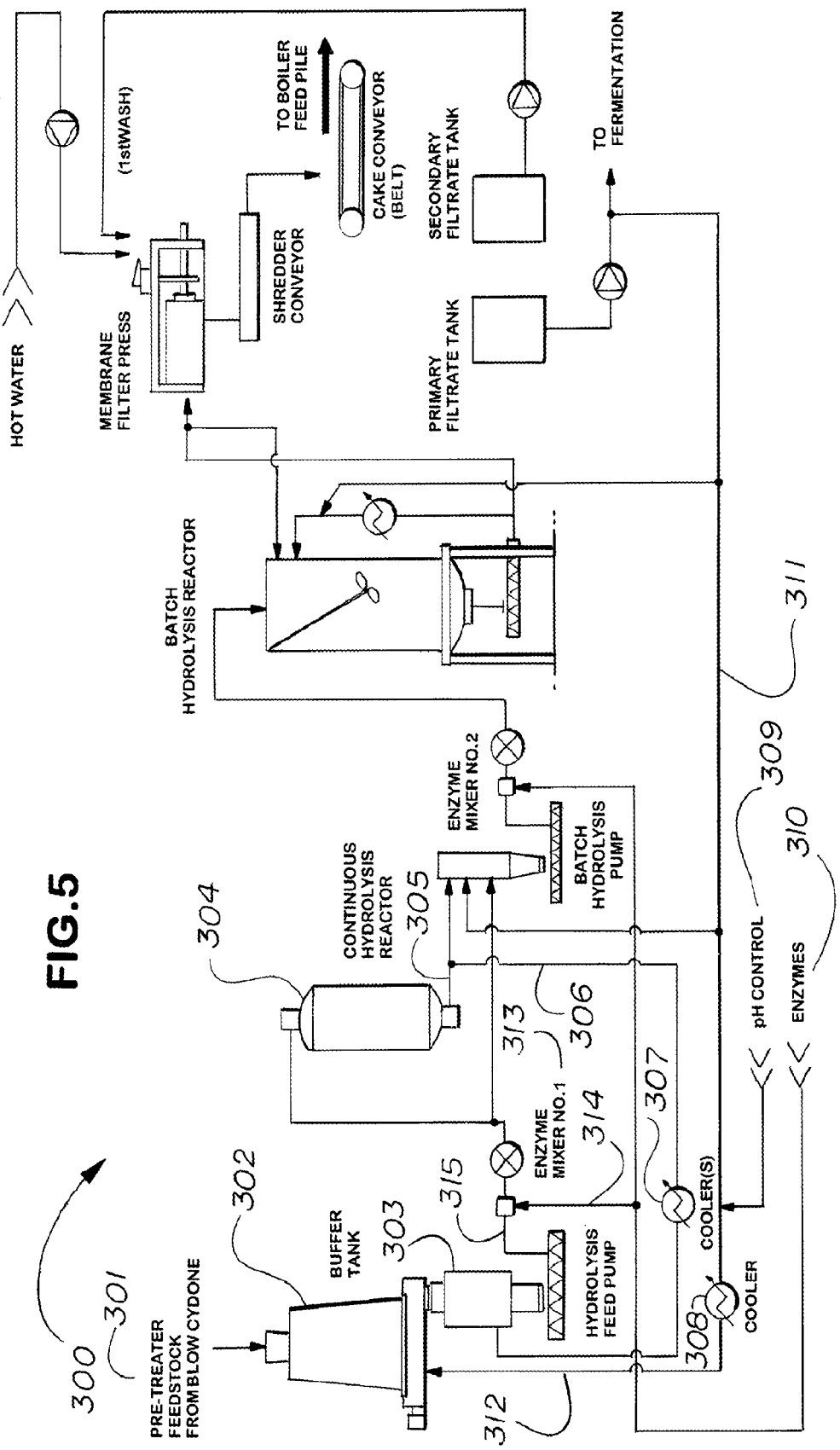
FIG. 5 depicts a process flow diagram of the overall process by which lignocellulosic materials are mixed with one or more enzymes or enzyme-containing solutions in an enzymatic hydrolysis reaction in order to produce monomeric sugars or other useful by-products using recirculated liquefaction material for cooling after the addition of pH controlling liquid.

FIG. 5 shows an additional embodiment of a process 300 of enzymatic hydrolysis of steam exploded biomass where pH control occurs prior to the addition of cooled liquefaction material from the enzymatic hydrolysis reactor.

Hot pretreated, steam exploded lignocellulosic material (biomass), feedstock 301, typically at a temperature greater than about 60° C., is fed to a buffer tank 302. Partial temperature adjustment and pH control is made to feedstock 301 by the addition of cooling material 312. Cooling material 312 may be water, or filtrate 311 from elsewhere within the process with the addition of pH controlling liquid 309 and may be cooled via heat exchanger or cooler 308. From the buffer tank 302, material is fed to the enzymatic hydrolysis feeding device 303 where at least a portion of the enzymatic hydrolyzed continuous reactor discharge 305 is fed via conduit 306 and cooler 307 to the enzymatic hydrolysis feeding device 303 to produce cooled reactor feedstock 315. The cooled reactor feedstock 315 is transferred to mixer 313 where enzyme solution via conduit 314 is added at or prior to a first enzyme mixer 313 to produce cooled reactor feedstock and enzyme mixture 316 for processing in at least one continuous enzymatic hydrolysis reactor 304 and/or further processing in additional enzymatic hydrolysis reactors, continuous or batch reactors. A portion of enzymatic hydrolyzed continuous reactor discharge 305 from continuous enzymatic hydrolysis reactor 304 is fed to other process equipment for further or subsequent enzymatic hydrolysis.

The flow system has been described herein as a continuous flow system.

Though the temperature or pH of the feedstock 301 may fluctuate slightly throughout the enzymatic hydrolysis process, it is advantageous for the temperature to remain under about 40° C. to 55° C. (or under about 50° C.), and the pH to remain in the range of about 4 to 6.5 (or about 4.5 to 6.5), in order to increase the enzyme performance, in certain example embodiments.

Figure 6:
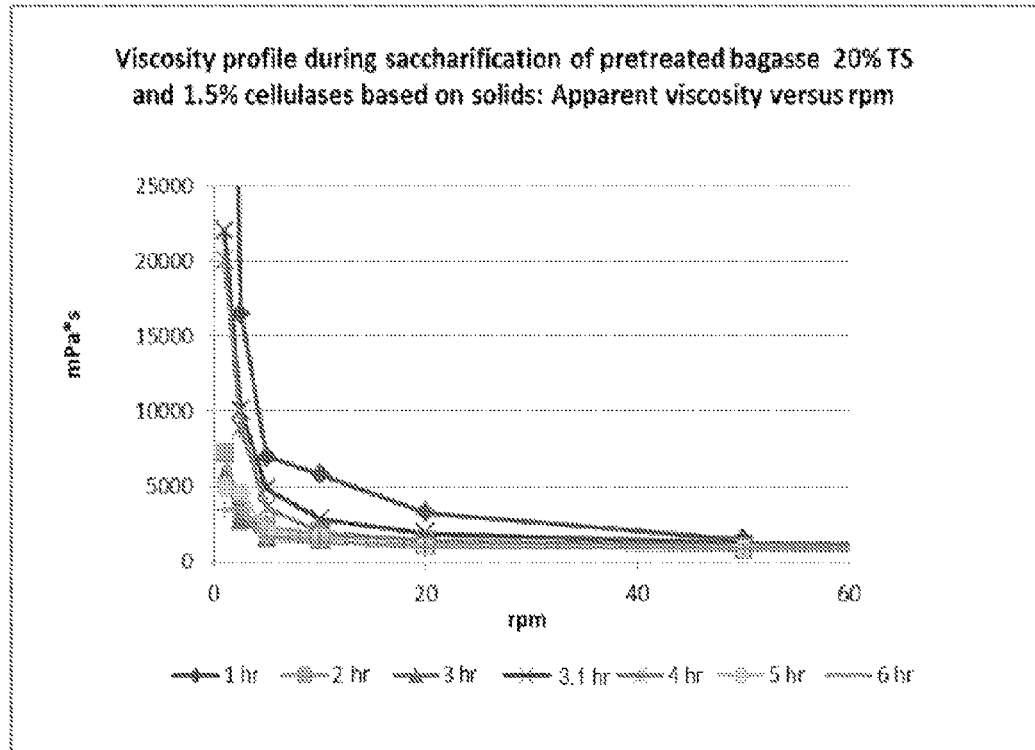
FIG. 6 depicts a line graph of the viscosity profile during saccharification of pretreated bagasse showing apparent viscosity versus rpm of the viscosity measuring device.

FIG. 6 is a line graph showing the relationship between apparent viscosity of the pretreated biomass, in this case bagasse, versus rpm of the mixing action within the viscosity testing device. The rpm used in the measurement of apparent viscosity is important to the measurement. In this application, apparent viscosity measurements use the well accepted Brookfield Viscometer with a cylindrical spindle, specifically the LV DV-II+ having 4 spindles and capable of operating at a speed of 0.1 to 200 revolutions per minute (rpm). The apparent viscosity measurements reported for purposes of this application were taken at 20 rpm.

Figure 7:
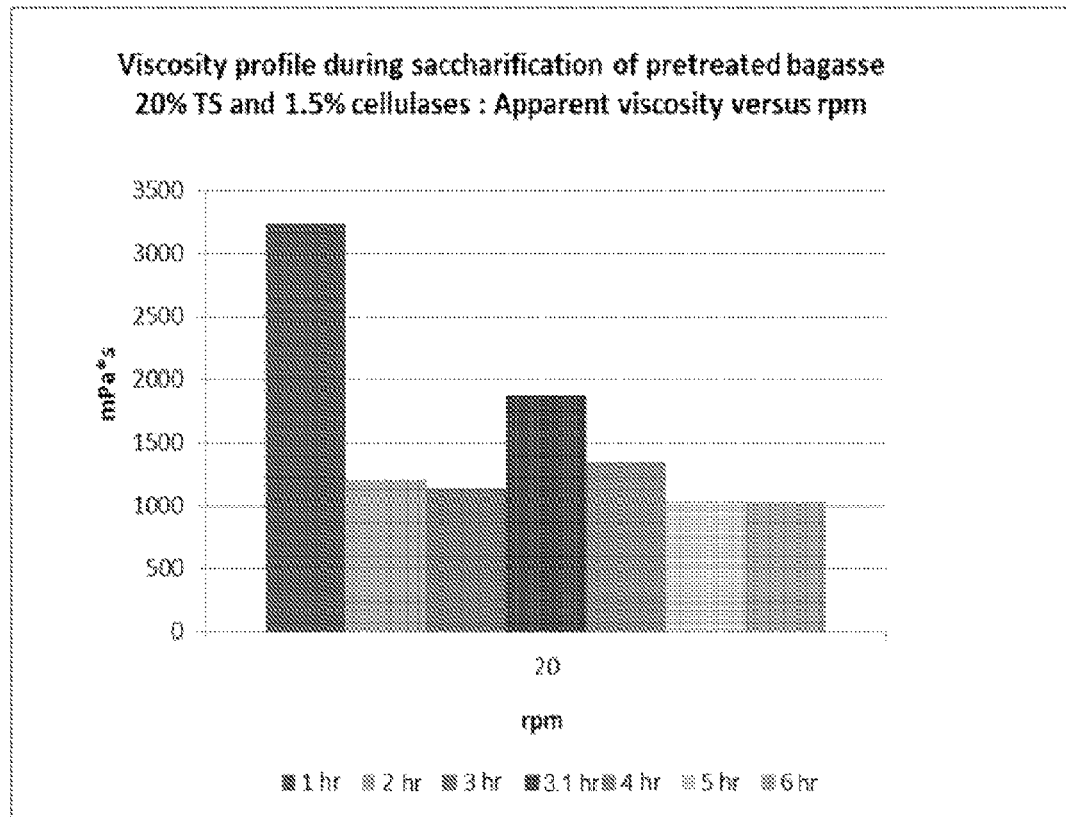
FIG. 7 depicts a bar graph of the viscosity profile during saccharification of pretreated bagasse showing apparent viscosity versus rpm of the viscosity measuring device.

FIG. 7 shows the apparent viscosity at various times during the enzymatic hydrolysis treatment phase, again bagasse is the biomass used for this study. The pretreated bagasse in the period of hours one to three does not include any recirculated liquefaction material. The first enzymatic hydrolysis reactor vessel has a three hour retention time with continuous operation, therefore material added at startup of the first enzymatic hydrolysis reactor vessel remains within the first enzymatic hydrolysis reactor vessel for three hours and can be considered the control sample. For the pretreated bagasse during the first three hours of operation, only cold water was added as the coolant material.

At hour one the apparent viscosity is above about 3,000 mPa·s, after three hours, the apparent viscosity remains above about 1,000 mPa·s and the liquefaction material discharged from the enzymatic hydrolysis reactor vessels is suitable for use as coolant, prior to use as coolant the liquefaction material is cooled, if necessary, to the desired temperature for coolant. After three hours of continuous operation (the first three hours being considered the control sample), a portion of the liquefaction material produced and discharged from the enzymatic hydrolysis reactor vessel was used as coolant for the pretreated bagasse fed to the enzymatic hydrolysis reactor vessel. The apparent viscosity of pretreated bagasse cooled with the recirculated liquefaction material was sampled at hour 3.1. A rise in the apparent viscosity occurs due to the solids content in the recirculated liquefaction material used as coolant being higher than the solids content of water used as the only coolant during the first 3 hours of operation. As operations continue to hour six, enzymatic hydrolysis of the pretreated bagasse also continues to produce liquefaction material. A sample of the liquefaction material after the six hour point was taken and the apparent viscosity determined to be about 1,000 mPa·s. The time period from the point where cooling liquid was changed from all water to at least a portion of the cooling liquid being liquefaction material, at hour 3.1 to hour six demonstrates the impact of recirculating liquefaction material. During this evaluation, the ratio of liquefaction material to non-liquefaction material ratio is 2.2. As shown in FIG. 7, the apparent viscosity at the three hour point (the control part of the test) is higher than the apparent viscosity at the six hour point, confirming the use of recirculated liquefaction material as at least a portion of the cooling liquid is advantageous to the process.

Figure 8:
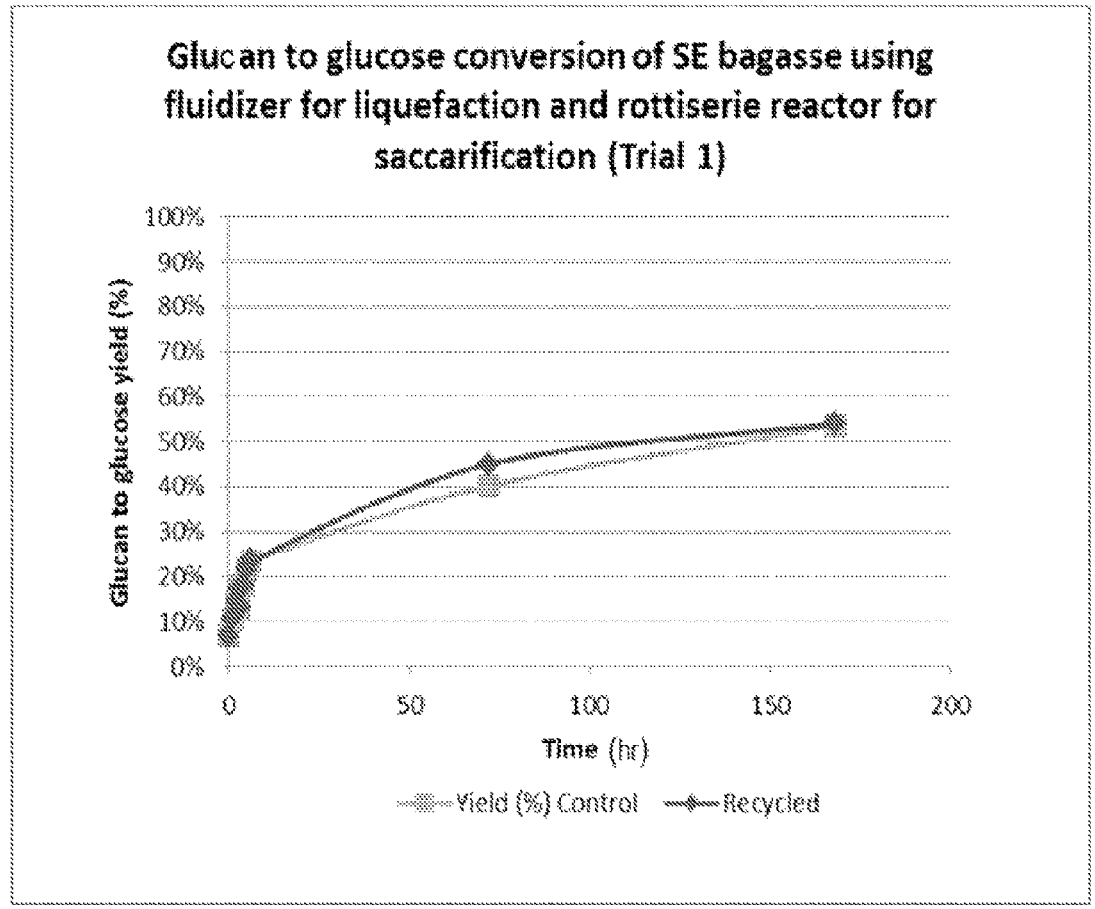
FIG. 8 depicts a line graph of glucan to glucose conversion Trial 1 comparing once through with recirculation of liquefaction material as coolant.

FIG. 8 shows a line graph of the conversion (yield percent) of glucan (cellulose) to glucose over time when enzymatic hydrolysis occurs. It is desirable to have a higher conversion, higher glucose yield percentage, over time, especially in the first 72 hour point of the process. Most industrial operations of enzymatic hydrolysis limit the total retention time for contact with the enzymes to about 72 hours. As shown in FIG. 8, the glucose yield percentage is higher when liquefaction material is recirculated and used as at least as a portion of the cooling liquid as compared to the control where only water is used as the cooling liquid.

Figure 9:
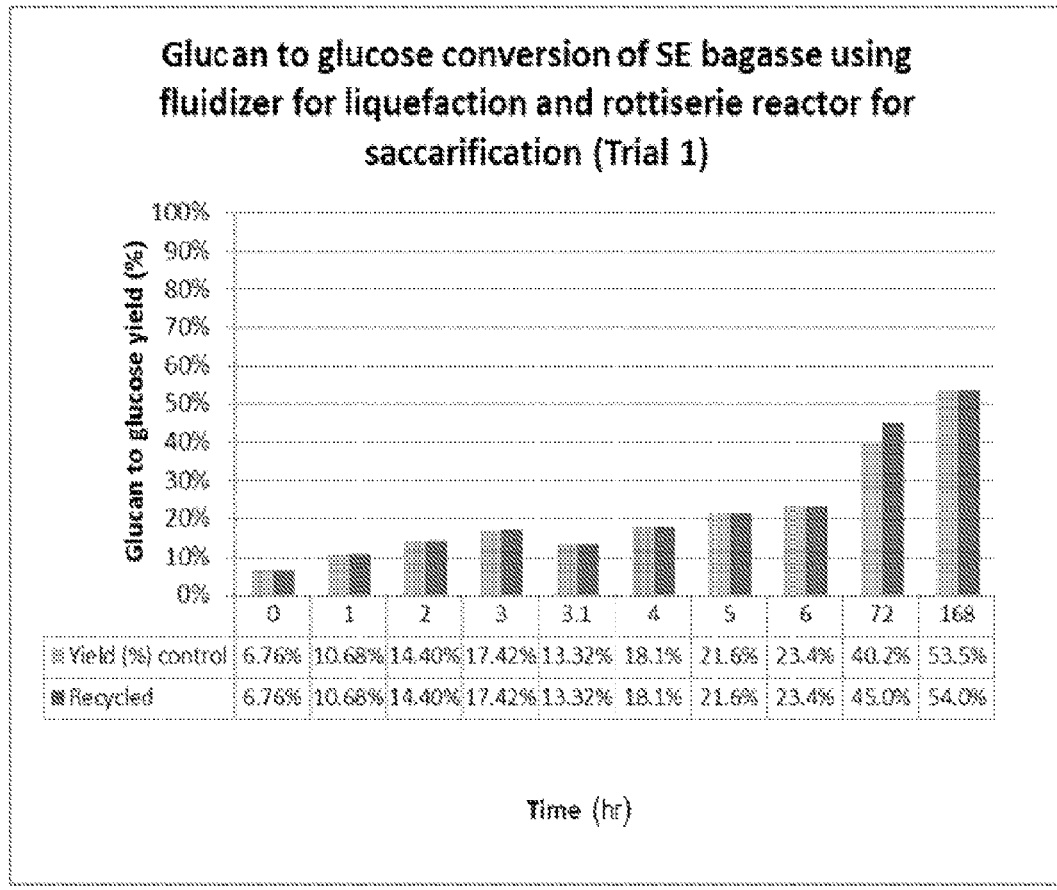
FIG. 9 depicts bar graph showing glucan to glucose conversion Trial 1 comparing once through with recirculation of liquefaction material as coolant.

FIG. 9 shows a bar graph and yield table corresponding to FIG. 8. This graph and glucose yield data (control versus recirculated cases discussed above) shows the glucose yield over time tracks closely for about the first 6 hours, but at about hour 72, the point where industrial enzyme hydrolysis of biomass typically is considered to be over, a glucose yield improvement of almost about 5% is realized from the process using at least a portion of the recirculated liquefaction material as coolant for the pretreated biomass.

Figure 10:
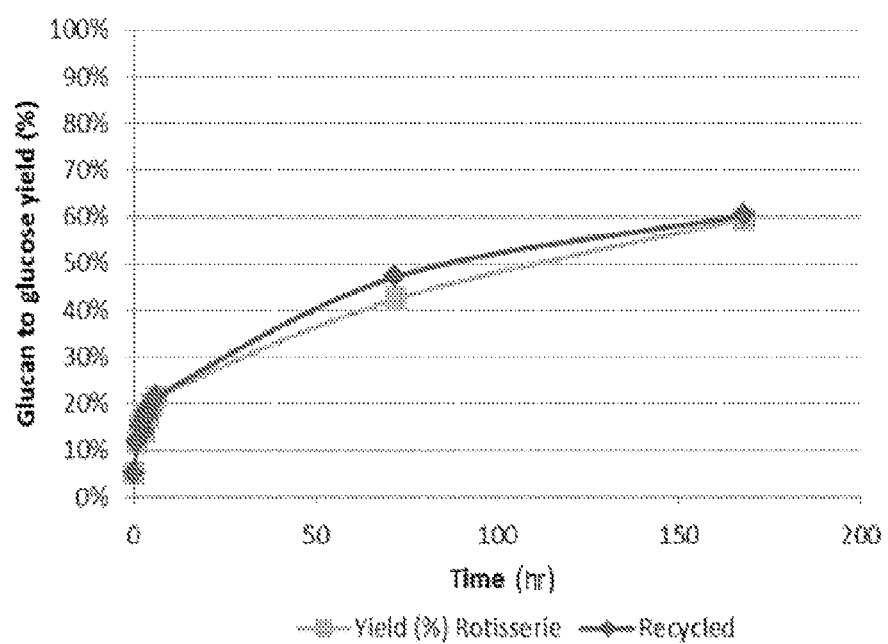
FIG. 10 depicts a line graph of glucan to glucose conversion Trial 2 comparing once through with recirculation of liquefaction material as coolant.
Figure 11:
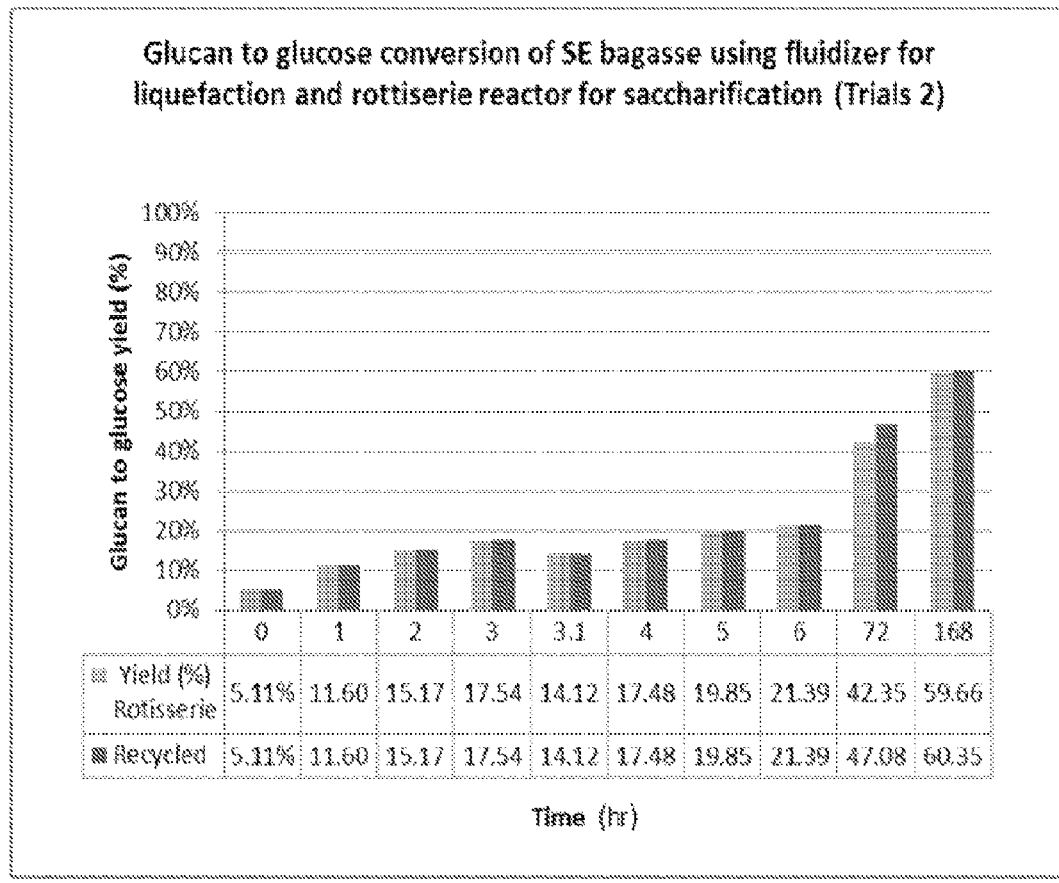
FIG. 11 depicts a bar graph of glucan to glucose conversion Trial 2, comparing once through with recirculation of liquefaction material as coolant.

FIG. 10 is a second trial run, again showing the glucose yield for early hours of enzyme hydrolysis for the control and recirculated liquefaction material operations tracking very closely, and a significant glucose yield improvement for the case using recirculated liquefaction material as at least a portion of the cooling liquid at about the 72 hour point. FIG. 11 shows the same information as FIG. 10 in bar graph form with an added yield table. At about the 72 hour point of enzyme hydrolysis, the glucose yield for the control case is almost about 5% lower than the glucose yield for the case where recirculated liquefaction material is used as at least a portion of the pretreated biomass cooling liquid.

It will be understood by all readers of this written description that the exemplary embodiments of the present disclosure may be suitably practiced in the absence of any element, step or feature that is, or is not, specifically disclosed herein.

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claims appended hereto unless otherwise claimed. No language in the specification should be construed as indicating any non-claimed element as essential.

Advantages and features of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiments and are intended to cover various modifications and equivalent arrangements included within the spirit and scope of the appended claims.

What is claimed is:

1. A enzymatic hydrolysis system for biomass material comprising:
   a pretreatment reactor for receiving a biomass material;
   a transfer system, in fluid communication with a discharge of the pretreatment reactor, capable of receiving a cooling liquid and a pH adjusting material, wherein the cooling liquid and the pH adjusting material mix with the biomass material to produce a cooled and pH controlled pretreated biomass, wherein the cooled and pH controlled pretreated biomass has a first apparent viscosity;
   an enzyme addition system in fluid communication with the transfer system for the addition of an enzyme solution, wherein the enzyme solution is introduced to the cooled and pH controlled pretreated biomass in the transfer system at an enzyme solution inlet;
   a first enzymatic hydrolysis vessel in fluid communication with the transfer system, wherein the first enzymatic hydrolysis vessel and the transfer system are disposed downstream of the discharge of the pretreatment reactor, wherein the enzyme solution reacts with the cooled and pH controlled pretreated biomass to produce a liquefaction material having a second apparent viscosity and and a concentration of monomeric glucose relative to polymeric cellulose of less than 30 percent;
   a recirculation conduit fluidly communicating with the first enzymatic hydrolysis vessel and transfer system, wherein the transfer system is disposed upstream of the first enzymatic hydrolysis vessel;
   a first portion of the liquefaction material, wherein the first portion of the liquefaction material moves from the first enzymatic hydrolysis vessel through the recirculation conduit to the pretreated biomass in the transfer system; and
   a cooling device in communication with the recirculation conduit, wherein the cooling device cools the first portion of the liquefaction material in the recirculation conduit before the first portion of the liquefaction material enters the transfer system, and wherein a second portion of the liquefaction material exits an outlet of the first enzymatic hydrolysis vessel to move downstream to a subsequent enzymatic hydrolysis reactor vessel, after the first portion of the liquefaction material enters the recirculation conduit, wherein the subsequent enzymatic hydrolysis reactor vessel produces a further hydrolyzed biomass.

2. The system of claim 1, wherein the transfer system includes a first conveyor, wherein the first conveyor passes the pretreated biomass from the discharge of the pretreatment reactor, and wherein the first conveyor further comprises an inlet configured to introduce a cooling liquid or pH controlling material or combination thereof to the pretreated biomass.

3. The system of claim 2, wherein the transfer system further comprises a second conveyor, or mixer, or combination thereof, and wherein the transfer system includes the enzyme solution inlet for introducing the enzyme solution to the cooled and pH controlled pretreated biomass.

4. The system of claim 3, wherein the mixer is in fluid communication with a discharge of the first conveyor or the second conveyor, wherein the mixer includes a mixing device rotating at a speed of about 400 rpm to about 4,000 rpm, and wherein the mixer retains the cooled and pH controlled pretreated biomass and the enzyme solution for about 0.05 seconds to about 200 seconds, and wherein the mixer includes the enzyme solution inlet configured to introduce the enzyme solution to the cooled and pH controlled pretreated biomass during mixing.

5. The system of claim 3, further comprising the mixer downstream of the first conveyor and fluidly communicating with the first conveyor, wherein the mixer has an enzyme solution inlet configured to receive the enzyme solution.

6. The system of claim 3 further comprising a second conveyor and a buffer tank for temporarily retaining the cooled and pH controlled pretreatment biomass from the second conveyor and discharging the cooled and pH controlled pretreated biomass to a transport device.

7. The system of claim 1, wherein the recirculation conduit fluidly communicates with the transfer system upstream of enzyme solution inlet and thereby introduces liquefaction material to the pretreated biomass in the transfer system upstream of the enzyme solution inlet.

8. The system of claim 1, wherein the subsequent enzymatic hydrolysis reactor vessel further comprises a plurality of subsequent reactor vessels, wherein each subsequent enzymatic hydrolysis reactor vessel is configured to receive the second portion of liquefaction material being transferred from the first enzymatic hydrolysis vessel.

9. The system of claim 1, wherein the first apparent viscosity of the cooled and pH controlled pretreated biomass is greater than 5,000 mPa·s.

10. The system of claim 1, wherein the second apparent viscosity the liquefaction material is less than 2,000 mPa·s.

11. The system of claim 1, wherein the further hydrolyzed biomass has a monomeric glucose content of 30 percent or more relative to the polymeric cellulose.

12. A process flow system, comprising:
a pretreating reactor vessel configured to pretreat biomass at a temperature of at least about 100° C.;
a cooling conduit configured to introduce cooling liquid to cool a continuous flow of the pretreated biomass to a temperature no greater than 80° C. in a transfer system in fluid communication with the pretreating reactor vessel and downstream of the pretreating reactor vessel;
a pH controlling device configured to add pH controlling material to the pretreated biomass in the transfer system;
a first enzymatic hydrolysis vessel configured to enzymatically hydrolyze the cooled and pH controlled pretreated biomass using an enzyme, yeast, thermophilic bacteria, mesophilic bacteria or other biological catalyst to produce a liquefaction material, wherein the liquefaction material has a concentration of monomeric glucose relative to polymeric cellulose of less than 30 percent;
a subsequent enzymatic hydrolyzing reactor vessel configured to enzymatically hydrolyze a second portion of the liquefaction material produced in the first enzymatic hydrolysis vessel, wherein the enzyme, yeast, thermophilic bacteria, mesophilic bacteria or other biological catalyst enzymatically hydrolyzes the second portion of the liquefaction material, wherein the subsequent enzymatic hydrolyzing reactor vessel is coupled to receive the second portion of the liquefaction material discharged from the first enzymatic hydrolysis vessel; and
a pump configured to transfer the first portion of the liquefaction material to a cooling device communicating with the pump, wherein the pump is in fluid communication with the first enzymatic hydrolysis vessel and the transfer system, wherein the transfer system is disposed upstream of the first enzymatic hydrolysis vessel, wherein the first portion of the liquefaction material enters the pump, and wherein the cooling device cools the first portion of the liquefaction material before the first portion of the liquefaction material enters the transfer system.

* * * * *